United States Patent
Baker et al.

(10) Patent No.: US 9,688,718 B2
(45) Date of Patent: Jun. 27, 2017

(54) NANOLIPOPROTEIN PARTICLES COMPRISING HYDROGENASES AND RELATED PRODUCTS, METHODS AND SYSTEMS

(75) Inventors: Sarah E. Baker, Pleasanton, CA (US);
Brett A. Chromy, Danville, CA (US);
Paul Henderson, Dublin, CA (US);
Paul D. Hoeprich, Jr., Pleasanton, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 290 days.

(21) Appl. No.: 12/352,472

(22) Filed: Jan. 12, 2009

(65) Prior Publication Data
US 2009/0186393 A1 Jul. 23, 2009

Related U.S. Application Data

(60) Provisional application No. 61/020,638, filed on Jan. 11, 2008, provisional application No. 61/115,446, filed on Nov. 17, 2008.

(51) Int. Cl.
| | | |
|---|---|---|
| C07K 1/14 | (2006.01) | |
| C12N 11/02 | (2006.01) | |
| B82B 1/00 | (2006.01) | |
| B82Y 5/00 | (2011.01) | |
| C12P 3/00 | (2006.01) | |

(52) U.S. Cl.
CPC .............. *C07K 1/145* (2013.01); *C12N 11/02* (2013.01); *C12P 3/00* (2013.01); *Y10S 977/799* (2013.01)

(58) Field of Classification Search
CPC . C07K 1/145; C12N 11/02; C12P 3/00; Y10S 977/799
See application file for complete search history.

(56) References Cited

U.S. PATENT DOCUMENTS

| | | | |
|---|---|---|---|
| 4,317,771 A | 3/1982 | Shiba et al. | |
| 5,393,530 A | 2/1995 | Schneider et al. | |
| 6,270,649 B1 | 8/2001 | Zeikus et al. | |
| 7,048,949 B2 | 5/2006 | Sligar et al. | |
| 7,083,958 B2 | 8/2006 | Sligar et al. | |
| 7,375,234 B2 | 5/2008 | Sharpless et al. | |
| 7,015,471 B2 | 8/2010 | Del Villar Fernandez et al. | |
| 8,183,010 B2 | 5/2012 | Swartz et al. | |
| 8,907,061 B2 | 12/2014 | Chromy et al. | |
| 9,303,273 B2 | 4/2016 | Hoeprich et al. | |
| 9,388,232 B2 | 7/2016 | Dasseux et al. | |
| 2004/0180369 A1 | 9/2004 | Franzen et al. | |
| 2005/0182243 A1 | 8/2005 | Sligar et al. | |
| 2005/0244414 A1 | 11/2005 | Mundy et al. | |
| 2006/0189554 A1 | 8/2006 | Mumper et al. | |
| 2006/0211092 A1 | 9/2006 | Sligar et al. | |
| 2007/0101448 A1 | 5/2007 | Anantharamiah et al. | |
| 2007/0117179 A1 | 5/2007 | Kudlicki et al. | |
| 2008/0124350 A1 | 5/2008 | Mumper et al. | |
| 2009/0136937 A1 | 5/2009 | Coleman et al. | |
| 2009/0186393 A1 | 7/2009 | Baker et al. | |
| 2009/0192299 A1 | 7/2009 | Chromy et al. | |
| 2009/0203549 A1 | 8/2009 | Hoeprich et al. | |
| 2009/0311276 A1 | 12/2009 | Hoeprich et al. | |
| 2010/0203609 A1* | 8/2010 | Yacoby et al. | 435/168 |
| 2011/0059549 A1* | 3/2011 | Coleman et al. | 436/501 |
| 2011/0178029 A1 | 7/2011 | Knudsen et al. | |
| 2011/0195450 A1 | 8/2011 | Kudlicki et al. | |
| 2012/0245101 A1 | 9/2012 | Anantharamaiah et al. | |

FOREIGN PATENT DOCUMENTS

| | | |
|---|---|---|
| JP | 2015110677 A | 6/2015 |
| WO | 0065099 | 11/2000 |
| WO | WO 02/40501 | 5/2002 |
| WO | WO 2004/094651 | 11/2004 |
| WO | 2004112214 A2 | 12/2004 |
| WO | 2005070400 | 8/2005 |
| WO | 2006073419 | 7/2006 |
| WO | 2007038755 | 4/2007 |
| WO | 2007/050501 | 5/2007 |
| WO | 2007/053655 | 5/2007 |
| WO | 2008028206 | 3/2008 |
| WO | WO 2008/106660 | 9/2008 |
| WO | 2009/100201 | 8/2009 |
| WO | 2010040897 A1 | 10/2009 |

OTHER PUBLICATIONS

Civjan, N.R., et al. 2003 BioTechniques 35(3): 556-559, 562-563.*
Persson, B., et al. 1996 Protein Science 5: 363-371.*
Baas, B.J., et al. 2004 Archives of Biochemistry and Biophysics 430: 218-228.*
Craig D. Blanchette et al., "Atomic Microscopy Differentiates Discrete Size Distributions Between Membrane Protein Containing and Empty Nanolipoprotein Particles," *Biochimica et Biophysica Acta;* vol. 1788, pp. 724-731 (2009; pre-published electronically on Dec. 8, 2008).
International Search Report for PCT/US2008/063307 filed on May 9, 2008 in the name of Lawrence Livermore National Security, LLC.
Written Opinion for PCT/US2008/063307 filed on May 9, 2008 in the name of Lawrence Livermore National Security, LLC.
International Preliminary Report on Patentability for PCT/US2008/063307 mailed on Nov. 19, 2009.
Dunn, R. J. et al., "Structure-functions studies on bacteriorhodopsin" Expression of the bacterio-opsin gene *Escherichia coli,* vol. 262, No. 19, pp. 9246-9254, Jul. 5, 1986.
Sonar, S et al., "Cell-Free Synthesis, Functional Refolding and Spectroscopic Characterization of Bacteriorhodopsin, an Integral Membrane Protein", Biochemistry, vol. 32, pp. 13777-13781, Oct. 25, 1993.

(Continued)

*Primary Examiner* — Marsha Tsay
(74) *Attorney, Agent, or Firm* — Steinfl + Bruno, LLP

(57) ABSTRACT

Provided herein are nanolipoprotein particles that comprise a membrane associated hydrogenase and related assemblies, devices, methods and systems.

23 Claims, 7 Drawing Sheets

(56) References Cited

OTHER PUBLICATIONS

Kalmbach, R., et al., "Functional Cell-free synthesis of a seven helix membrane protein: In situ Insertion of Bacteriorhodopsin in Liposomes", J. Mol. Biol. vol. 371, pp. 639-648, 2007.

Wang, J., et al., "Comparison of the Dynamics of the primary events of bacteriorhodopsin in Its trimeric and monomeric states", Biophysical Journal, vol. 83, pp. 1557-1566, Sep. 2002.

Bayburt, T. H., et al., "Assembly of single bacteriorhodopsin trimers in bilayer nandiscs", Archives of Biochemistry and Biophysics, pp. 215-222, 2006.

Chromy, B. A., et al., "Different Apolipoproteins Impact Nanolipoprotein Particle Formation", J. Am. Chem. Soc., vol. 129, pp. 14348-14354, Oct. 27, 2007.

Bayburt, T. H., et al., "Reconstitution and Imaging of a Membrane Protein in a Nanometer-Size Phospholipid Bilayer" Journal of Structural Biology, pp. 37-44, 1998.

Forstner, M., et al., "Carboxyl-Terminal domain of Human Apolipoprotein E: Expression, Purification, and Crystallization", Protein Expression and Purification, vol. 17, pp. 267-272, 1999.

Morrow, J. A., et al., "Functional Characterization of Apolipoprotein E Isoforms Overexpressed in *Escherichia coli*", Protein Expression and Purification, vol. 16,pp. 224-230, 1990.

Jayaraman, S., et al., "Structural Basis for Thermal Stability of Human Low-Density Lopoprotein", Biochemistry 44, pp. 3965-3971, 2005.

Gursky, O., et al., Compex of Human Apolipoprotein C-1 with Phospholipid: Thermodynamic or Kinetic Stability? Biochemistry 41, pp. 7373-7384, 2002.

Coleman, M., et al., "Asp 46 can substitute for Asp 96 as the Schiff Base Proton Donor in Bacteriorhodopsin", Biochemistry 34, pp. 15599-15606, 1995.

Klammt, C., et al., "High level cell-free expression and specific labeling of integral membrane proteins", Eur. J. Biochem, 271, pp. 568-580, 2004.

Klammt, C., et al., "Cell-free expression as an emerging technique for the large scale production of integral membrane protein" FEBS Journal, 273, pp. 4141-4153, 2006.

Sonar, S., et al., "A redirected proton pathway in the bacteriorhodopsin Mutan Tyr-57→Asp", The Journal of Biological Chemistry, vol. 269, No. 46, pp. 28851-28858, Nov. 18, 1994.

Klammt, C., et al., "Evaluation of detergents for the soluble expression of α-helical and β-barrel-type integral membrane proteins by a preparative scale individual cell-free expression system", FEBS Journal, pp. 6024-6038, 2005.

Camarero, J. A., et l., "Chemoselective Attachment of Biologically Active Protein to Surfaces by Expressed Protein Ligation and Its Application for Protein Chip Fabrication", J.A. Chem. Soc., vol. 126, pp. 14730-14731, 2004.

Rao, R.S., et al., "Comparison of Multiplexed techniques for detection of bacterial and Viral Proteins", Journal of Proteome Research, 3, pp. 736-742, 2004.

Segelke, B. W., et al., "Laboratory scale structural genomics", Journal of Structural and Functional Genomics 5, pp. 147-157, 2004.

Lu, B., et al., "Conformational reorganization of the four-helix bundle of human apolipoprotein E in Binding to Phospholipid", The Journal of Biological Chemistry, vol. 275, No. 27, pp. 20775-20781, Jul. 7, 2000.

Wientzek, M., et al., "Binding of Inspect Apolipophorin III to Dimyristoylphosphatidylcholine Vesicles", The Journal of Biological Chemistry, vol. 269, No. 6, pp. 4605-4612, 1994.

Forte T.M., "Electron microscope study on reassembly of plasma high density apoprotein with various lipids", Biochimi. Biophys. Acta, 248, pp. 381-386, 1971.

Abdulreda, M.H, Atomic Force Microscope Spectroscopy Reveals a Hemifusion Intermediate during Soluble N-Ethylmaleimide Sensitive Factor-Attachment Protein Receptors-Mediated Membrane Fusio, Biophysical Journal,vol. 94, pp. 648-655, Jan. 2008.

PCT International Search Report for PCT/US2008/063307 filed on Sep. 5, 2008 in the name of Lawrence Livermore National Security, LLC.

PCT Written Opinion for PCT/US2008/063307 filed on Sep. 5, 2008 in the name of Lawrence Livermore National Security, LLC.

Bayburt, T. H., et al., "Self-assembly of single integral membrane proteins into soluble nanoscale phospholipid bilayers", Protein Science vol. 12, No. 11, Nov. 2003 (Nov. 2003), pp. 2476-2481.

Goldet, G.; Wait, A. F.; Cracknell, J. A,; Vincent, K. A.; Ludwig, M.; Lenz, Friedrich, B.; Armstrong, F. A. , "Hydrogen Production under Aerobic Conditions by Membrane-Bound Hydrogenases from Ralstonia Species", *Journal of the American Chemical Society* 2008, 130, (33),1, 1106-1113.

Cracknell, J. A.; Vincent, K. A.; Ludwig, M.; Lenz, 0.; Friedrich, B.; Armstrong, F. A., "Enzymatic oxidation of H2 in Atmosphere O2", Journal of the American Chemical Society 2007, 130,424-425.

Kovacs, K. L.; Maroti, G.; Rakhely, G., "A novel approach for biohydrogen production", *International Journal of Hydrogen Energy* 2006, 31, (1 I), 1460-1468.

Ho, D.; Chu, B.; Lee, H.; Brooks, E. K.; Kuo, K.; Montemagno, C. D., "Fabrication of biomolecule-copolymer hybrid nanovesicles as energy conversion systems", *Nanotechnology* 2005, 16, (12), 3120-3132.

Vincent, K. A.; Cracknell, J. A,; Lenz, 0.; Zebger, I.; Friederich, B.; Armstrong, F., "Electrocatalytic hydrogen oxidation by an enyme at high carbon monoxide or oxygen levels", *Proceedings of the National Academy of Sciences* 2005,102, (47),16951-16954.

Zhang, Y.-H. P.; Evans, B. R.; Mielenz, J. R.; Hopkins, R. C.; Adams, M. W. W. "High-Yield Hydrogen Production from Startch and Water by a Synthetic Enzymatic Pathway", *PLoS ONE* 2007, e456, (S), 1-6.

Sanderson, K., "The photon trap", *Nature* 2008, 452, 400-402.

Woodward, J.; Mattingly, S. M.; Danson, M.; Hough, D.; Ward, N.; Adams, M. "In vitro hydrogen production by glucose dehydrogenase and hydrogenase", *Nature Biotechnology* 1996, 14,872-874.

Woodward, J.; Orr, M.; Cordray, K.; Greenbaum, E., "Enzymatic production of biohydrogen", *Nature* 2000, 405, 1014-1015.

Elgren, T. E.; Zadvomy, O. A.; Brecht, E.; Douglas, T.; Zorin, N. A,; Maroney, M. J.; Peters, "Immobilization of Active Hydrogenases by Encapsulation in polymeric porous gels", *Nano Letters* 2005 vol. 5, No. 10 2085-2087.

Bayburt, T. H.; Grinkova, Y. V.; Sligar, S. G. , "Self-assembly of discoidal phospholipid bilayer nanoparticles with membrane scaffold proteins", *Nano Letters,:* 2002, 2, (8),853-856.

Borch, J. et al., "Nanodiscs for immobilization of Lipid Bilayers and Membrane Receptors:", *Analytical Chemistry* 2008,80, (16), 6245-6252.

Blanchette, C. D.; Law, R.; Benner, W. H.; Pesavento, J. B.; Cappuccio, J. A,; Walsworth, V. L.; Kuhn, E. A,; Corzette, M.; Chromy, B. A,; Segelke, B. W.; Coleman, M. A,; Bench, G.; Hoeprich, P. D.; Sulcheck, T. A. "Quantifying Distributions . . . ", *Journal of Lipid Research* 2008,49, (7), 1420-1430.

Chromy, B. A.; Arroyo, E.; Blanchette, C. D.; Bench, G.; Benner, H.; Cappuccio, J. A,; Coleman, M. A.; Henderson, P. T.; Hinz, A. K.; Kuhn, E. A.; Pesavento, J. B.; Segclke, B. W.; Sulcheck, T. A.; Tarasow, T.; Walsworth, V. L.; Hoeprich, P. D., "Different Apolipoproteins Impact Nanolipoprotein Particle Formation", *Journal of the American Chemical Society* 2007, 129, 14348-14354.

Nath, A,; Atkins, W. M.; Sligar, S. G. "Applications of Phospholipid . . . ", Biochemistry 2007,46, (8), 2059-2069.

Boldog, T.; Grimme, S.; Li, M.; Sligar, S.; Hazelbauer, G. L. "Nanodiscs separate chemoreceptor oligomeric states and reveal their signaling properties," *Proceedings of the National Academy of Sciences* 2006, 103, (31), I1509-11514.

Leitz, A. J.; Bayburt, T. H.; Basnakov, A. N.; Springer, B. A,; Sligar, S. G., "Functional reconstitution of B2-adrenergic receptors utilizing self-assembling Nanodisc technology", *Biotechniques* 2006, 40, (5), 60 1-6 12.

Hedderich, R., "Energy-Converting [NiFi] Hydrogenases From Archaea and Extremophiles", *Journal of Bioenergetics and Biomembranes* 2004, 36, (1), 65-75.

(56) References Cited

OTHER PUBLICATIONS

Vignais PM. ; Billoud B. Ocurrence, Classification, and Biological Function of Hydrogenases: An overview. *Chemical Reviews* 2007, 107, 4206-4272.
Jed O. Eberly and Roger L. Ely, "Thermotolerant Hydrogenases", *Critical Reviews in Microbiology*, 34:117-130, 2008.
Sun, X. et al . Membrane-Mimetic Films of Aymmetric Phosphtidylcholine Lipid Bolaamphiphiles. *Langmuir* 2006,22, 1201-1208.
Meyer, J. "Fe/Fe hydrogenases and their evolution: a genomic perspective." Cell. Mol. Life. Sci. 64 2007 1063-1084.
Vincent, K. A. et al. "Investigating and Exploiting the Electrocatalytic Properties of Hydrogenases" Chern. Rev. 2007 107, 4366-4413.
Parkin, A., Goldet, G. Cavazza, C. Fontecilla-Camps, J., Armstrong, F. J., "The difference a Se Makes?", Am Chern. Soc. 2008,13 (40) 13410-13416.
North P. and Fleischer S. "Alteration of Synaptic Membrane Cholesterol/Phospholipid Ratio Using a Lipid Transfer Protein", (1983) J. Biol. Chem. vol. 258, No. 2. pp. 1242-1253.
Bockaert J., Brand C., Journot, L. (1997), Do Recombinant Receptor Assays Provide Affinity and Potency. In Receptor Classification: The integration of operational, structural, and transductional information (D.G. Trist, P.P.A. Humphrey, P. Leff, and N.P. Shankley, Eds.). vol. 812. New York, New York Academy of Sciences.
Tufteland M. et al., "Peptide Stabilized Amphotericin B nanodisks", Peptides (2007) 28:741-748.
Jonas, A. "Reconstitution of High-Density Lipoproteins", Methods Enzymol. 1986, 128, 553-82.
J. Wang, S. Link, C.D. Heyes and M.A. El-Sayed, Comparison of the dynamics of the primary events of bacteriorhodopsin in its trimeric and monomeric states, Biophys. J. 83 (2002), pp. 1557-1566.
G. Bacher, R. Korner, A. Atrih, S.J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of peptidoglycan fragments isolated from various *Bacillus* species, J. Mass Spectrom. 36 (2001), pp. 124-139.
Sapra R et al, "Purification and characterization of a Membrane-Bound Hydrogenase from the Hyperthermophilic Archaeon Pyrococcus furiosus", J Bacteriol. 2000 182, (12) 3423-3428.
Sapra R et al, "A simple energy-conserving system: Proton reduction coupled to proton translocation", J Bacteriol 2003, 100 (13), 7545-7550.
Pasini EM et al., In depth analysis of the membrane and cytosolic proteome of red blood cells, 2006 Blood, 108: 791-801.
G. Bacher et al., "Charge-reduced nano electrospray ionization combined with differential mobility analysis of peptides, proteins, glycoproteins, non covalent protein complexes and viruses", Journal of Mass Spectrometry 2001; 36: 1038-1052.
Restriction Requirement issued for U.S. Appl. No. 12/352,548, filed Jan. 12, 2009 in the name of Brett A. Chromy et al.; mail date: Apr. 25, 2011.
Restriction Requirement issued for U.S. Appl. No. 12/118,530, filed May 9, 2008 in the name of Matthew A. Coleman et al.; mail date: Sep. 24, 2010.
Restriction Requirement issued for U.S. Appl. No. 12/118,530, filed May 9, 2008 in the name of Matthew A. Coleman et al.; mail date: Mar. 30, 2011.
Restriction Requirement issued for U.S. Appl. No. 12/118,396, filed May 9, 2008 in the name of Matthew A. Coleman et al.; mail date: Mar. 4, 2011.
Chefson, A. et al. Progress towards the easier use of P450 enzymes, *Mol. bioSyst.*, 2006, 2, 462-469.
Sapra, R. et al., Purification and Characterization of a Membrane-Bound Hydrogenase from the Hyperthermophilic Archaeon *Pyrococcus furiosus*, Journal of Bacteriology, Jun. 2000, vol. 182, No. 12, pp. 3423-3428.

Lubert Stryer et al., Oxygen Binds to a Heme Prosthetic Group, Biochemistry 1995, 4th edition, 148.
Wuu, J., et al., High yield cell-free production of integral membrane proteins without refolding or detergents, BBA 2008, 1778: 1237-1250.
Final Office Action for U.S. Appl. No. 12/118,530, filed May 9, 2008 in the name of Matthew A. Coleman et al., mail date: Jan. 25, 2012.
Notice of Allowance for U.S. Appl. No. 12/352,548, filed Jan. 9, 2009 in the name of Brett A. Chromy et al., mail date: Mar. 12, 2012.
Final Office Action for U.S. Appl. No. 12/118,396, filed May 5, 2008 in the name of Matthew A. Coleman et al., mail date: Jan. 18, 2012.
Bayburt, T.H. et al. Self-assembly of single integral membrane proteins into soluble nanoscale phospholipid bilayers, *Nano Letters* 2002 vol. 2, pp. 853-856.
Bockaert, J. et al. Do Recombinant Receptor Assays Provide Affinity and Potency Estimates? In Receptor Clssification: The integration of operational, structural, and transductional information (D.G. Trist, P.P.A. Humphrey, P. Leff, and N.P. Shankley, Eds.) *Annals New York Academy of Sciences*, 1997, vol. 812, pp. 55-70.
Cullis P.R. et al. Physical Properties and Functional Roles of Lipids in membranes, *Biochemistry of Lipids, Lipoproteins and Membranes*, 1991, Chapter 1, pp. 1-41.
Silvius, J.R. Thermotropic Phase Transitions of Pure Lipids in Model Membranes and Their Modification by Membrane Proteins, *Lipid-Protein Interactions*, 1982, vol. 2 pp. 239-281.
Non-Final Office Action issued for U.S. Appl. No. 12/352,548, filed Jan. 12, 2009 in the name of Brett A. Chromy et al.; mail date: Sep. 13, 2011.
Non-Final Office Action issued for U.S. Appl. No. 12/118,530, filed May 9, 2008 in the name of Matthew A. Coleman et al.; mail date: Aug. 30, 2011.
Non-Final Office Action issued for U.S. Appl. No. 12/118,396, filed May 9, 2008 in the name of Matthew A. Coleman et al.; mail date: Aug. 30, 2011.
Gorrod, JW, et al., Some observations on Type I and Type II microsomal binding spectra, Xenobiotica 1971, 1: 521-522.
Chen, JS, et al., Amino acids in SRS1 and SRS6 are critical for furanocoumarin metabolism by CYP6B1v1, a cytochrome P450 monooxygenase, Insect Mol. Biol. 2002, 11: 175-186.
Das, D., et al., Role of Fe-hydrogenase in biological hydrogen production, Current Science 2006, 90: 1627-1637.
Gilbert, L., Insect Development: morphognesis and metamorphosis, Academic Press, Sep. 2009, pp. 573-574.
Definition of Hydrogenase retrieved from en.wikipedia.org/wiki/Hydrogenase on Nov. 6, 2012, pp. 1-4.
Advisory Action mailed on Jun. 6, 2012 for U.S. Appl. No. 12/118,530, filed May 9, 2008 in the name of Matthew A. Coleman et al.
Advisory Action mailed on Jun. 7, 2012 for U.S. Appl. No. 12/118,396, filed May 9, 2008 in the name of Matthew A. Coleman et al.
Lodish, H., et al., Section 17.5 Insertion of Membrane Proteins, Molecular Cell Biology 4th ed. 2000, New York, NY.
White, SH, et al., How Translocons Select Transmembrane Helices, Annu. Rev. Biophys. 2008, 37: 23-42.
Petrakova, O., Volkova, E., Gorchako, R., Paessler, S., Kinney, R.M., and Frolov, I., Noncytopathic replication of Venezuelan equine encephalitis virus and eastern equine encephalitis virus replicons in Mammalian cells. J Virol 79, 7597-608 (2005).
Konishi, E., and Mason, P.W., Proper maturation of the Japanese encephalitis virus envelope glycoprotein requires co-synthesis with the premembrane protein. J Virol 67, 1672-5 (1993).
Widman, D. G., Ishikawa, T., Fayzulin, R., Bourne, N., Mason, P.W., Construction and characterization of a second-generation pseudoinfectious West Nile virus vaccine propagated using a new cultivation system. Vaccine 26, 2762-71 (2008).
Fischer, N., et al., Immobilization of His-Tagged Proteins on Nickel-Chelating Nanolipoprotein Particles. Bioconjugate Chemistry 20, 460-5 (2009).

(56) References Cited

OTHER PUBLICATIONS

Terpe, K., Overview of tag protein fusions: from molecular and biochemical fundamentals to commercial systems. Appl Microbiol Biotechnol, 60, 523-33 (2003).
Kolb, H. and Sharpless, B., The growing impact of click chemistry on drug discovery. Drug Discov. Today, 8, 1128-37 (2003).
Martin, B.R. and Cravatt, B.F., Large-scale profiling of protein palmitoylation inmammalian cells. Nat. Methods 6, 135-38 (2009).
T. Gardner et al. "Systems for Orthogonal Self-Assembly of Electroactive Monolayers on Au and ITO: An Approach to Molecular Electronics," JACS 1995, 117:6927-6933.
G.H. McGall et al. "The Efficiency of Light-Directed Synthesis of DNA Arrays on Glass Substrates," J. Amer. Che. Soc. 1997, 119:5081-5090.
M.A. Schena et al. "Quantitative Monitoring of Gen Expression Patterns with a Complementary DNA Microarray," Science, 1995, 270:467-470.
S. Singh-Gasson et al. "Maskless fabrication of light-directed oligonucleotide microarrays using a digital micromirror array," Nature Biotech. 1999, 17:974-978.
Simon, S.R. and Konigsberg, W.H., Chemical modification of hemoglobins: a study of conformation restraint by internal bridging. Proc. N.A.S. USA, 56, 749-56 (1966).
Hein, C.D., Liu, X-M, and Wang, D. 2008. Click Chemistry, A Powerful Tool for Pharmaceutical Sciences. Pharmaceutical Research, vol. 25, No. 10:2216-2230.
Dalpke, A.H., Zimmermann, S., Albrecht, I. & Heeg, K. 2002. Phosphodiester CpG oligonucleotides as adjuvants: polyguanosine runs enhance cellular uptake and improve immunostimulative activity of phosphodiester CpG oligonucleotides in vitro and in vivo. Immunology 106:102-112.
Weermata, R.D., McCluskie, M.J., Xu, Y., and Davis, H.L. 2000. CpG DNA induces stronger immune responses with less toxicity than other adjuvants. Vaccine 18:1755-62.
Ueda H et al., Induction of tumor necrosis factor-a in solid tumor region by the orally administered synthetic muramyl dipeptide analogue, romurtide (2001) Int'l Immunopharm. 1:97-104.
Osada Y et al., Polymorphonuclear Leukocyte Activation by a Synthetic Muramyl Dipeptide Analog (1982) Inf. Immun. 38:848-854.
Huleatt, J.W., Nakaara, V., Desaia, P., Huanga, Y., Hewitta,D., Jacobs, A., Tanga, J., McDonald, W., Song, L., Evans, R.K., Umlauf, S., Tussey, L., and Powell, T.J. 2008. Potent immunogenicity and efficacy of a universal influenza vaccine candidate comprising a recombinant fusion protein linking influenza M2e to the TLR5 ligand flagellin Vaccine 26:201-214.
Hamdy, S., Haddadi, A., Somayaji, V., Ruan, D. and Samuel, J. 2007. Pharmaceutical analysis of synthetic lipid A-based vaccine adjuvants in poly (d,l-lactic-co-glycolic acid) nanoparticle formulations. Journal of Pharmaceutical and Biomedical Analysis 44:914-923.
Giannini, S.L., Hanona, E., Moris, P., Van Mechelen, M., Morel, S., Dessy, F., Fourneau, M.A., Colau, B., Suzich, J., Losonksy, G., Martin, M-T., Dubin G., Wettendorff, M.A. 2006. Enhanced humoral and memory B cellular immunity using HPV16/18 L1 VLP vaccine formulated with the Mpl/aluminium salt combination (AS04) compared to aluminium salt only. Vaccine 24:5937-5949.
Fitzgerald, K.A. and Golenbock, D.T. 2007. The Shape of Things to Come. Science 316:1574-1576.
Behrens S., et al., Linking Microbial Phylogeny to Metabolic Activity at the Single-Cell Level by Using Enhanced Element Labeling-Catalyzed Reporter Deposition Fluorescence In Situ Hybridization (EL-FISH) and NanoSIMS, Appl. Environ. Microbiol. 2008, 74: 3143-3150.
Radajewski S., et al., Identification of active methylotroph populations in an acidic forest soil by stable isotope probing, Microbiol. 2002, 148: 2331-2342.
Manefield , M., et al., RNA Stable Isotope Probing, a Novel Means of Linking Microbial Community Function to Phylogeny, Applied and environmental microbiology, 2002, 68: 5367-5373.

Uhlik O., et al., DNA-based stable isotope probing: a link between community structure and function, Science of the Environ. 2009, 407: 3611-3619.
Addison SL, et al., Stable isotope probing: Technical considerations when resolving 15N-labeled RNA in gradients, J. Microbiol. Methods 2010, 80: 70-75.
Boschker HTS, et al., The contribution of macrophyte-derived organic matter to microbial biomass in salt-marsh sediments: Stable carbon isotope analysis of microbial biomarkers, Limnol. Oceanogr. 1999, 44: 309-319.
Ouverney C., et al., Combined Microautoradiography-16S rRNA Probe Technique for Determination of Radioisotope Uptake by Specific Microbial Cell Types In Situ, Applied and environmental microbiology 1999, 65: 1746-1752.
Adamczyk, J., et al., The Isotope Array, a New Tool That Employs Substrate-Mediated Labeling of rRNA for Determination of Microbial Community Structure and Function, Applied and environmental microbiology 2003, 69: 6875-6887.
Brodie EL et al., Application of a High-Density Oligonucleotide Microarray Approach to Study Bacterial Population Dynamics during Uranium Reduction and Reoxidation, Applied and environmental microbiology 2006, 72: 6288-6298.
Cline MS et al., Integration of biological networks and gene expression data using Cytoscape, Nat. Protocols 2007, 2: 2366-2382.
Ludwig W et al., ARB: a software environment for sequence data, Nuc. Acids Res. 2004, 32: 1363-1371.
PCT International Search Report mailed on Oct. 28, 2010 for PCT/US09/44722 filed on May 20, 2009 in the name of Lawrence Livermore National Security, LLC.
PCT Written Opinion mailed on Oct. 28, 2010 for PCT/US09/44722 filed on May 20, 2009 in the name of Lawrence Livermore National Security, LLC.
Bijsterbosch MK et al., Specific targeting of a lipophilic prodrug of iododeoxyuridine to parenchymal liver cells using lactosylated reconstituted high density lipoprotein particles, Biochem. Pharma 1996, 52: 113-121.
Jasanada F et al., Indium-111 labeling of low density lipoproteins with the DTPA—Bis(stearylamide): Evaluation as a Potential Radiopharmaceutical for Tumor Localization, Biocon. Chem. 1996, 7: 72-81.
Masquelier M et al., Low-density lipoprotein as a carrier of antitumoral drugs: in vivo fate of drug-human low-density lipoportien complexes in mice, Cancer Res. 1986, 46: 3842-3847.
PCT International Search Report mailed on Sep. 30, 2009 for PCT/US09/33193 filed on Feb. 5, 2009 in the name of Lawrence Livermore National Security, LLC.
PCT Written Opinion mailed on Sep. 30, 2009 for PCT/US09/33193 filed on Feb. 5, 2009 in the name of Lawrence Livermore National Security, LLC.
Brodie E et al., Profiling microbial identity and activity: Novel applications of NanoSIMS and High Density Microarrays, Systems Biology Research Strategy & Technology Development, Genomics: GTL Awardee Workshop VI, Dept. of Energy 2008, 93-94.
Non-Final Office Action mailed on Jul. 24, 2014 for U.S. Appl. No. 12/118,530, filed May 9, 2008 in the name of Matthew A. Coleman et al.
Non-final Office Action mailed on Jul. 22, 2014 for U.S. Appl. No. 12/118,396, filed May 9, 2008 in the name of Matthew A. Coleman et al.
Rusinol AE et al., In Vitro Reconstitution of Assembly of Apolipoprotein B48-containing Lipoproteins, J. Biol. Chem. 1997, 272: 8019-8025.
Walter P et al., Preparation of Microsomal Membranes for Cotranslational Protein Translocation, Methods in Enzymology 1983, 96: 84-93.
NTC of Allowance mailed on Apr. 25, 2014 for U.S. Appl. No. 12/352,548, filed Jan. 12, 2009 in the name of Brett A. Chromy et al.
NTC of Allowance mailed on Aug. 5, 2014 for U.S. Appl. No. 12/352,548, filed Jan. 12, 2009 in the name of Brett A. Chromy et al.

(56) References Cited

OTHER PUBLICATIONS

Restriction Requirement mailed on Jun. 7, 2011 for U.S. Appl. No. 12/469,533, filed May 20, 2009 in the name of Paul D. Hoeprich et al.
Non-Final Office Action mailed on Oct. 24, 2011 for U.S. Appl. No. 12/469,533, filed May 20, 2009 in the name of Paul D. Hoeprich et al.
Patel J et al., Preparation and Characterization of Nickel Nanoparticles for Binding to His-tag Proteins and• Antigens, Pharma. Res. 2007, 24: 343-352.
Schmitt L et al., Synthesis and Characterization of Chelator-Lipids for Reversible Immobilization of Engineered Proteins at Self-Assembled Lipid Interfaces, J. Am. Chem. Soc. 1994, 116: 8485-8491.
Final Office Action mailed on Dec. 4, 2012 for U.S. Appl. No. 12/469,533, filed May 20, 2009 in the name of Paul D. Hoeprich et al.
Ruger R et al., In vitro characterization of binding and stability of single-chain Fv Ni-NTA-liposomes, J. Drug Targeting 2006, 14: 576-582.
Ntc of Allowance mailed on Jul. 3, 2014 for U.S. Appl. No. 12/469,533, filed May 20, 2009 in the name of Paul D. Hoeprich et al.
Schnell DJ et al., Protein Translocons: Multifunctional Review Mediators of Protein Translocation across Membranes, Cell 2003, 112: 491-505.
"Assembly of nanodiscs for use in cell-free expression using MSP1D1 protein and POPC phospholipids." Cube Biotech. 3 pgs. 2014.
"Co-Translation of integral membrane proteins (MP) with membrane scaffold proteins (MSP), also known as nanodiscs" http://technology.sbkb.org/portal/page/329/ retrieved on Jul. 1, 2015, pp. 1-3.
"Nanodisc Assembly Kit MSP1E3D1_POPC" Cube Biotech, Dec. 2014, pp. 1-3.
"Nanodisc Formation" LIAO Lab, Department of Cellbiology, Harvard Medical School, http://liao.hms.harvard.edu/node/34; retrieved on Aug. 3, 2015.
"Nanodisc" Kobo eBook Library, http://www.kobolibrary.com/articles/Nanodisc, retrieved on Aug. 4, 2015, pp. 1-4.
"Protocols for Preparation of Nanodiscs" Mar. 4, 2008, pp. 1-7.
5-HT Receptor, Wikipedia 2007, http://web.archive.org/web/20071109235348/http://en.wikipedia.org/wiki/5-HT_receptor.
Adrenergic Receptor, Wikipedia 2006, http://web.archive.org/web/20061230132111/http://en.wikipedia.org/wiki/Adrenergic_Receptor.
Author Unknown, Special Report, Dengue fever climbs the social ladder, Nature, 2007, vol. 448, pp. 734-735.
Barros, F., et al., Modulation of human erg K+ channel gating by activation of a G protein-coupled receptor and protein kinase C, J. Physiology 1998, 511: 333-346.
Beja, O. et al. Bacterial Rhodopsin: Evidence for a New Type of Phototrophy in the Sea, Science, 2000, 2895.5486: 1902-1906.
Bischler, N. et al., Specific Interaction and Two-Dimensional Crystallization of Histidine Tagged Yeast RNA Polymerase I on Nickel-Chelating Lipids, Biophysical Journal, Mar. 1998, vol. 74, pp. 1522-1532.
Blanchette, C.D., et al., Characterization and Purification of Polydisperse Reconstituted Lipoproteins and Nanolipoprotein Particles. International Journal of Molecular Sciences 2009, 10:2958-2971.
Boroske et al. "Osmotic Shrinkage of Giant Egg-Lecithin Vesicles" Biophys. J. 1981, 34, 95-109.
Chaung, et al., CpG oligodeoxynucleotides as DNA adjuvants in vertebrates and their applications in immunotherapy (2006) Int'l Immunopharm. 6:1586-1596.
Chikh, et al., Attaching histidine-tagged peptides & proteins to lipid-based carriers through use of metal-ion-chelating lipids (2002) BBA 1567:204-212.
Choquet et al. "Stability of pressure-extruded liposomes made from archaeobacterial ether lipids" Appl. Microbiol. Biotechnol. 1994, 42, 375-384.
Crankshaw, C. "Nanodisc Technology: A Revolutionary System for Study of Membrane Proteins" Biofiles, vol. 8, No. 20, http://www.sigmaaldrich.com/technical-documents/articles/biofiles/nanodisc-technology.html; pp. 1-3 Retrieved on Aug. 4, 2015.
Dawson P. et al. "Synthesis of Native Proteins by Chemical Ligation" (2000), Ann Rev Biochem 69: pp. 923-960.
Disalvo et al. "Surface changes induced by osmotic shrinkage on large unilamellar vesicles" Chem. Phys. Lipids 1996, 84, 35-45.
Dong, F., et al., Endothelin-1 enhances oxidative stress, cell proliferation and reduces apoptosis in human umbilical vein endothelial cells: role of ETB receptor, NADPH oxidase and caveolin-1 British J. of Pharmacology 2005, 145: 323-333.
Dumartin, B., et al., Dopamine tone regulates D1 receptor trafficking and delivery in striatal neurons in dopamine transporter-deficient mice, PNAS 2000, 97: 1879-1884.
Fischer et al. "Conjugation to Nickel-Chelating Nanolipoprotein Particles Increases the Potency and Efficacy of Subunit Vaccines to Prevent West Nile Encephalitis" Bioconjugate Chemistry 2010, 21: pp. 1018-1022.
Fischer, N. et al. "Evaluation of Nanolipoprotein Particles (NLPs) as an In Vivo Delivery Platform" PLoS ONE 9(3): e93342, Mar. 1-17, 2014.
G Protein-coupled Receptor, Wikipedia 2008, http://web.archive.org/web/20080224232212/http://en.wikipedia.org/wiki/G_protein-coupled_receptor.
Gantz, I., et al.,Molecular cloning of a gene encoding the histamine H2 receptor, PNAS 1991, 88: 429-433.
Gupta, R., et al., Adjuvants for human vaccines—current status, problems and future prospects, Vaccine 1995, 13: 1263-1276.
Hauger, R., et al., Corticotropin Releasing Factor (CRF) Receptor Signaling in the Central Nervous System: New Molecular Targets, CNS Neurol. Discord. Drug Target 2006, 5: 453-479.
Hernández-Caselles et al. "Influence of liposome charge and composition on their interaction with human blood serum proteins" Mol. Cell. Biochem. 1993, 120, 119-126.
Hong, Y., et al., G-Protein-Coupled Receptor Microarrays for Multiplexed Compound Screening J. Biomol. Screening 2006, 11: 435-438.
Jones, M. et al."Computer programs to identify and classify amphipathic helical domains" Journal of Lipid Research, vol. 33, pp. 287-296, 1992.
Kostarelos et al. "Steric stabilization of phospholipid vesicles by block copolymers: Vesicle Flocculation and osmotic swelling caused by monovalent and divalent cations" J. Chem. Soc., Faraday Trans., 1998, 94, 2159-2168.
Kubalek, E.W. et al., Two-Dimensional Crystallization of Histidine-Tagged, HIV-1 Reverse Transcriptase Promoted by a Novel Nickel-Chelating Lipid, Journal of Structural Biology, 1994, vol. 113, pp. 117-123.
Lam, K. S., "Application of combinatorial library methods in cancer research and drug discovery" Anticancer Drug Des. (1997) pp. 145-167.
Lasic et al. "Novel Applications of Liposomes" Trends Biotechnol. 1998, 16, 307-321.
Liang et at "Mechanical properties and stability measurement of cholesterol-containing liposome on mica by atomic force microscopy" J. Colloid Interface Sci. 2004, 278, 53-62.
Mata-Haro, V., et al., The vaccine adjuvant monophosphoryl lipid A as a TRIF-biased agonist of TLR4, Science 2007, 316: 1628-1632.
Metz, J., et al ACTH, a-MSH, and control of cortisol release: cloning, sequencing, and functional expression of the melanocortin-2 and melanocortin-5 receptor in Cyprinus carpio Am. J. Physiol. Regul. Integr. Comp. Physiol. 2005, 289: R814-R826.
Okemoto, K., et al., A Potent Adjuvant Monophosphoryl Lipid A Triggers Various Immune Responses, but Not Secretion of IL-1β or Activation of Caspase-1, The Journal of Immunology 2006, 176: 1203-1208.
Persing, D., et al., Taking toll: lipid A mimetics as adjuvants and immunomodulators, Trends in Microbiology 2002, 10: S32-S37.

(56) References Cited

OTHER PUBLICATIONS

Pettibone, D., et al., The Effects of Deleting the Mouse Neurotensin Receptor NTR1 on Central and Peripheral Responses to NeurotensinJ. Pharma. & Exp. Therapeutics 2002, 300: 305-313.

Radajewski et al., Stable-isotope probing as a tool in microbial ecology. Nature 403, 646-649 (2000).

Ratanabanangkoon, P. et al., Two-Dimensional Streptavidin Crystals on Giant Lipid Bilayer Vesicles, Langmuir, 2002, vol. 18, pp. 4270-4276.

Ren, X., et al Different G protein-coupled receptor kinases govern G protein and b-arrestin-mediated signaling of V2 vasopressin receptor, PNAS 2005, 102: 1448-1453.

Ruger, et al., Generation of immunoliposomes using recombinant single-chain Fv fragments bound to Ni-NTA-liposomes (2005) J. Drug Targeting 13:399-406.

Shih, et al. Molecular Dynamics Simulations of Discoidal Bilayers Assembled from Truncated Human Lipoproteins. Biophysical J. 2006, 88: 548-556.

Sperling, et al. "Surface modification, functionalization and bioconjugation of colloidal inorganic nanoparticles". Phil. Trans. R. Soc. A (2010) vol. 368 No. 1915 pp. 1333-1383.

Stryer "Lipid Vesicles (Liposomes) and Planar Membranes are Valuable Model Systems" Biochemistry, 4th Ed. W.H. Freeman and Company, New York: 1995, p. 271.

Ulmer, et al., Vaccine manufacturing: challenges and solutions (2006) Nature Biotech. 24:1377-1383.

Wetterau & A. Jonas, "Effect of Dipalmitoylphosphatidylcholine Vesicle Curvature on the Reaction with Human Apolipoprotein A-I", The Journal of Biological Chemistry, 1982, 257:10961-10966.

Whorton M. et al. "A monomeric G protein-coupled receptor isolated in a high-density lipoprotein particle efficiently activates its G protein" Proc Natl Acad Sci US A 104, 7682-7.

Yoon et al. "Three-Dimensional Graphene Nano-Networks with High Quality and Mass Production Capability via Precursor-Assisted Chemical Vapor Deposition" Scientific Reports (2013) 3:1788, 1-8.

Zimmermann, et al., Immunostimulatory DNA as adjuvant: efficacy of phosphodiester CpG oligonucleotides is enhanced by 3' sequence modifications (2003) Vaccine 21:990-995.

Notice of Allowance for U.S. Appl. No. 14/199,973, filed Mar. 6, 2014 on behalf of Paul D. Hoeprich. Mail Date: Dec. 10, 2015. 11 pages.

Advisory Action for U.S. Appl. No. 12/118,530, filed May 9, 2008 on behalf of Matthew A. Coleman. Mail Date: Jul. 23, 2015. 13 pages.

Advisory Action for U.S. Appl. No. 12/118,396, filed May 9, 2008 on behalf of Matthew A. Coleman. Mail Date: Jul. 7, 2015. 8 pages.

Non-Final Office Action for U.S. Appl. No. 12/118,396, filed May 9, 2008 on behalf of Matthew A. Coleman. Mail Date: Jan. 8, 2016. 32 pages.

Non-Final Office Action for U.S. Appl. No. 14/536,513, filed Nov. 7, 2014 on behalf of Brett A. Chromy. Mail Date: Mar. 24, 2016. 19 pages.

Baker et al., "Hydrogen Production by a Hyperthermophilic Membrane-Bound Hydrogenase in Water Soluble Nanolipoprotein Particles" (2009), J. Amer. Chem. Soc., 131 (2):7508-7509. (15 pages).

Bayburt, T. H., and Sligar, S. G. (2002) "Single-molecule height measurements on microsomal cytochrome P450 in nanometer-scale phospholipid bilayer disks", Proc Natl Acad Sci U S A, 99, 6725-6730.

Bayburt, T. H., Leitz, A. J., Xie, G., Oprian, D. D., and Sligar, S. G. (2007) "Transducin activation by nanoscale lipid bilayers containing one and two rhodopsins", J Biol Chem, 282 (20), 14875-14881.

Boschker et al., "Direct linking of microbial populations to specific biogeochemical processes by 13C-labelling of biomarkers", Nature, 392, 801-805 (1998).

Brodie et al., "Urban aerosols harbor diverse and dynamic bacterial populations". Proceedings of the National Academy of Sciences 104 (1), 299-304 (Jan. 2, 2007).

Cappucchio J. et al., "Cell-free Co-expression of Functional Membrane Proteins and Apolipoprotein, Forming Soluble Nanolipoprotein Particles", Molecular and Cellular Proteomics 7.11 (2008) pp. 2246-2253.

Casey P.J.; M. C. Seabra, (1996). "Protein Prenyltransferases". Journal of Biological Chemistry 271 (10): 5289-5292.

Christian Schulze Gronover, Daniela Wahler and Dirk Prefer (2011). "Natural Rubber Biosynthesis and Physic—Chemical Studies on Plant Derived Latex" in Biotechnology of Biopolymers, Magdy Elnashar (Ed.), ISBN: 978-953-307-179-4. pp. 75-88.

Cornish & J.J. Blakeslee, "Rubber Biosynthesis in Plants", American Oil Chemist Society, The Lipid Library, Nov. 2, 2011. 10 pages.

Cornish, K. et al., "Natural Rubber Biosynthesis in Plants: Rubber Transferase" Methods in Enzymology, (2012) vol. 515, pp. 63-82.

Cruz, F., and Edmondson, D. E. (2007) "Kinetic properties of recombinant MAO-A on incorporation into phospholipid nanodisks", J Neural Transm, 114, 699-702.

DeSantis et al., "Greengenes, a Chimera-Checked 16S rRNA Gene Database and Workbench Compatible with ARB", Appl. Environ. Microbiol. 72 (7), 5069-5072 (2006).

DeSantis et al., "High-Density Universal 16S rRNA Microarray Analysis Reveals Broader Diversity than Typical Clone Library When Sampling the Environment", Microbial Ecology 53, 371-383 (2007).

Donniger & G. Popjak, "An Improved Synthesis of Isopentenyl Pyrophosphate", (1967) Biochem. J. 105:545-547.

Frydman, J., and Hartl, F. U. (1996) "Principles of chaperone-assisted protein folding: differences between in vitro and in vivo mechanisms", Science 272, 1497-1502.

Greve, "Ullman's Encyclopedia of Industrial Chemistry, Rubber, 2. Natural", 2012, Wiley-VCH Verlag GmbH & Co., KGaA, Weinheim, DOI: 10.1002/14356007.a23_225, pp. 583-596.

Hiraishi, Tomohiro; Taguchi, Seiichi "Enzyme-catalyzed Synthesis and Degradation of Biopolymers", Mini-Reviews in Organic Chemistry, vol. 6, No. 1, Feb. 2009, pp. 44-54(11) Bentham Science Publishers.

Ishihara, G., Goto, M., Saeki, M., Ito, K., Hori, T., Kigawa, T., Shirouzu, M., and Yokoyama, S. (2005) "Expression of G protein coupled receptors in a cell-free translational system using detergents and thioredoxin-fusion vectors", Protein Expr Purif 41, 27-37.

Jonas, A., Kezdy, K. E., and Wald, J. H. (1989) "Defined apolipoprotein A-I conformations in reconstituted high density lipoprotein discs", J Biol Chem 264, 4818-4824.

Katzen et al. "Insertion of Membrane Proteins into Discoidal Membranes using a Cell-free Protein Expression Approach" (2008) J. Proteome Res., vol. 7, No. 8, 3535-3542; ASAP Article; DOI: 10.1021/pr800265f.

Lechene et al., "High-resolution quantitative imaging of mammalian and bacterial cells using stable isotope mass spectrometry" Journal of Biology (2006) 5:20, published on line at the http://pagejbiol.com/content/5/6/20. 30 pages.

Ohya; T. Koyama, (2001). "Biosynthesis of Natural Rubber and Other Natural Polyisoprenoids". Biopolymers Polyisoprenoids. 2, 73-81.

Paterson-Jones, M.G. Gilliland, J. Van Staden, "The Biosynthesis of Natural Rubber", Journal of Plant Physiology, vol. 136, Issue 3, Jun. 1990, pp. 257-263.

Peters-Libeu, C. A., Newhouse, Y., Hatters, D. M., and Weisgraber, K. H. (2006) "Model of biologically active apolipoprotein E bound to dipalmitoylphosphatidylcholine", J Biol Chem 281 (2), 1073-1079.

Cornish, K, Siler, DJ. "Characterization of cis-prenyl transferase activity localized in a buoyant fraction of rubber particles from Ficus elastica latex", Plant Physiol. Biochem. 1996; 34 (3): 377-384.

Ponciano et al. "Transcriptome and gene expression analysis in cold-acclimated guayule (Parthenium argentum) rubber-producing tissue", (2012) Phytochemistry 79:57-66.

Rensen P.C.N. et al., "Recombinant Lipoproteins: Lipoprotein-Like Lipid Particles for Drug Targeting" (2001) Adv. Drug Delivery Reviews. Elsevier, 47:251-276.

Sawasaki, T., Hasegawa, Y., Tsuchimochi, M., Kamura, N., Ogasawara, T., Kuroita, T., and Endo, Y. (2002) "A bilayer cell-free

(56) References Cited

OTHER PUBLICATIONS protein synthesis system for high-throughput screening of gene products", *FEBS Lett* 514, 102-105.
Schmidt et al. "Characterization of rubber particles and rubber chain elongation in *Taraxacum koksaghyz*", (2010) BMC Biochemistry 11:1-11.
Shaw, A. W., McLean, M. A., and Sligar, S. G. (2004) "Phospholipid phase transitions in homogeneous nanometer scale bilayer discs", *FEBS Lett* 556, 260-4.
Siler et al. "Composition of rubber particles of *Hevea brasiliensis, Parthenium argentatum, Ficus elastics* and *Euphorbia lactiflua* indicates unconventional surface structure" (1997) Plant Physiol. Biochem. 35 (11):881-889.
Singh et al, "The micromorphology and protein characterization of rubber particles in *Ficus carica, Ficus benghalensis* and *Hevea brasiliensis*" in Journal of Experimental Botany vol. 54, No. 384, pp. 985-992, Mar. 2003.
Stadermann, R. M. Walker, E. Zinner, "Nanosims: The Next Generation Ion Probe for Microanalysis of Extraterrestraisl Material", *Meteoritics & Planetary Science* 34 (4), A111-112 (Jul. 1999).
Vuorilehto et al., "Indirect electrochemical reduction of nicotinamide coenzymes", Bioelectrochemistry 65 (2004) 1-7.
Wallin, E., and von Heijne, G. (1998) "Genome-wide analysis of integral membrane proteins from eubacterial, archaean, and eukaryotic organisms", *Protein Sci* 7, 1029-1038.
Whalen et al, "Chapter 23: Development of Crops to Produce Industrially Useful Natural Rubber" of T.J. Bach and M. Rohmer (eds.), Isoprenoid Synthesis in Plants and Microorganisms: New Concepts and Experimental Approaches, Springer Science+Business Media New York, 2013. 329-345.
Xie, W.,; C. M. McMahan; A.J. DeGraw' M. D. Distefano; K. Cornish; M. C. Whalen; D. K. Shintani, "Initiation of rubber synthesis: In vitro comparisons of benzophenone modified diphosphate analogues in three rubber producing species", Phytochemistry, 69 (2008) 2539-2545.
Zhiqiang Pan, Francis Durst§, Daniele Werck-Reichhart§, Harold W. Gardner, Bilal Camarall, Katrina Cornish, and Ralph A. Backhausi, "The Major Protein of Guayule Rubber Particles is a Cytochrome P450", The Journal of Biological Chemistry, vol. 270, No. 15, Apr. 14, 1995, pp. 8487-8494.
Final Office Action issued for U.S. Appl. No. 12/118,530, filed May 9, 2008 in the name of Matthew A. Coleman. Mail date: Mar. 6, 2015.
Sun et al. "Overview of Protein Structural and Functional Folds", Current Protocols in Protein Science 2004, vol. 35, pp. 17.1.58-17.1.59.
Lee et al. "Ab lnitio Protein Structure Prediction", in From Protein Structure to Function with Bioinformatics, © Springer Science+Business Media B.V. 2009, pp. 3-25.
Aranyi et al. "Predictable difficulty or difficulty to predict", Protein Science, 2011, vol. 20, pp. 1-3.
Final Office Action issued for U.S. Appl. No. 12/118,396, filed May 9, 2008 in the name of Matthew A. Coleman. Mail date: Feb. 4, 2015.
Non-Final Office Action issued for U.S. Appl. No. 12/469,533, filed May 20, 2009 in the name of Paul D. Hoeprich. Mail date: May 23, 2012.
Restriction Requirement issued for U.S. Appl. No. 12/366,476, filed Feb. 5, 2009 in the name of Paul D. Hoeprich. Mail date: Sep. 23, 2011.
Non-Final Office Action issued for U.S. Appl. No. 12/366,476, filed Feb. 5, 2009 in the name of Paul D. Hoeprich. Mail date: Nov. 15, 2011.
Moses et al., "Detection of DNA hybridization on indium tin oxide surfaces", Sensors and Actuators B, 125 (2007) 574-580.
Brewer et al., "Formation of Thiolate and Phosphonate Adlayers on Indium-Tin Oxide: Optical and Electronic Characterization", Langmuir, 18 (2002) 6857-6865.
Brown et al., "Exploring the new World of the Genome with DNA microarrays", Nature Genetics, 1999,21 :33-37.

Bao et al., "High-Sensitivity Detection of DNA Hybridization on Microarrays Using Resonance Light Scattering", Anal. Chem., 2002, 74:1792-1797.
Non-Final Office Action issued for U.S. Appl. No. 12/366,476, filed Feb. 5, 2009 in the name of Paul D. Hoeprich. Mail date: Apr. 23, 2012.
Final Office Action issued for U.S. Appl. No. 12/366,476, filed Feb. 5, 2009 in the name of Paul D. Hoeprich. Mail date: Oct. 16, 2012.
Restriction Requirement issued for U.S. Appl. No. 12/604,362, filed Oct. 22, 2009 in the name of Paul D. Hoeprich. Mail date: Jan. 11, 2012.
Non-Final Office Action issued for U.S. Appl. No. 12/604,362, filed Oct. 22, 2009 in the name of Paul D. Hoeprich. Mail date: May 7, 2012.
Final Office Action issued for U.S. Appl. No. 12/604,362, filed Oct. 22, 2009 in the name of Paul D. Hoeprich. Mail date: Dec. 4, 2012.
Notice of Allowance issued for U.S. Appl. No. 12/604,362, filed Oct. 22, 2009 in the name of Paul D. Hoeprich. Mail date: Jul. 30, 2014.
Restriction Requirement issued for U.S. Appl. No. 13/023,468, filed Feb. 8, 2011 in the name of Jennifer Pett-Ridge. Mail date: Aug. 31, 2012.
Non-Final Office Action issued for U.S. Appl. No. 13/023,468, filed Feb. 8, 2011 in the name of Jennifer Pett-Ridge. Mail date: Oct. 26, 2012.
Brodie et al., "Profiling Microbial Identity and Activity: Novel Applications of NanoSIMS and High Density Microarrays", Systems Biology Research Strategy and Technology Developments. Abstract. Publicly disclosed on Feb. 13, 2008, http://genomicscience.energy.gov/pubs/2008abstracts/2008GTLabstracts_tech.pdf.
Kim et al., "Gold Nanoparticle-Enhanced Secondary Ion Mass Spectrometry Imaging of Peptides on Self-Assembled Monolayers", Anal. Chem., 78 (6), (2006), p. 1913-1920.
Restriction Requirement issued for U.S. Appl. No. 14/199,973, filed Mar. 6, 2014 in the name of Paul D. Hoeprich. Mail date: Dec. 8, 2014.
Non-Final Office Action issued for U.S. Appl. No. 14/199,973, filed Mar. 6, 2014 in the name of Paul D. Hoeprich. Mail date: May 6, 2015.
Unger et al., "The Genetic Algorithm Approach to Protein Structure Prediction", Structure and Bonding (2004) 110: 153-175.
Guo et al., "Protein tolerance to random amino acid change", 2004, Proc. Natl. Acad. Sci. USA 101 (25): 9205-9210.
Lazar et al., "Transforming Growth Factor α: Mutation of Aspartic Acid 47 and Leucine 48 Results in Different Biological Activities", 1988, Mol. Cell. Bioi. 8 (3):1247-1252.
Hill et al., "Functional Analysis of conserved Histidines in ADP-Glucose Pyrophosphorylase from *Escherichia coli*", 1998, Biochem. Biophys. Res. Comm 244:573-577.
Wacey et al., "Disentangling the perturbational effects of amino acid substitutions in the DNA-binding domain of p53", Hum Genet, 1999, vol. 104, pp. 15-22.
Berthelot et al., "Rubber Elongation Factor (REF), a Major Allergen Component in *Hevea brasiliensis* Latex Has Amyloid Properties", PLoS One (Epub Oct. 25, 2012), vol. 7 (10), pp. 1-12.
Cornish, "Biochemistry of natural rubber, a vital raw material, emphasizing biosynthetic rate, molecular weight and compartmentalization, in evolutionarily divergent plant species", Nat. Prod. Rep., (2001), vol. 18, pp. 182-189.
Cornish et al., "Natural Rubber biosynthesis in Plants: Rubber Transferase", Methods in Enzymology (2012), vol. 515, pp. 63-82.
Branden and Tooze, "Introduction to Protein Structure" (1999), 2nd edition, Garland Science Publisher, pp. 3-12.
Lluis et al., "Protein Engineering Methods Applied to Membrane Protein Targets" (2013) 26 (2): 91-100.
Boldog et al., "Using Nanodiscs to Create Water-Soluble Transmembrane Chemoreceptors Inserted in Lipid Bilayers", Methods in Enzymology, vol. 423, 317-335 (2007).
Burgdorf et al., "The Soluble NAD+-Reducing [NiFe]-Hydrogenase from *Ralstonia eutropha* H16 Consists of Six Subunits and Can Be Specifically Activated by NADPH", Journal of Bacteriology, 187 (9), 3122-3132 (2005).

(56) References Cited

OTHER PUBLICATIONS

Das et al., "Hydrogen production by biological processes: a survey of literature", International Journal of Hydrogen Energy, 26 (2001), 13-28.

Duan et al., "Co-incorporation of heterologously expressed *Arabidopsis* cytochrome P450 and P450 reductase into soluble nanoscale lipid bilayers", Archives of Biochemistry and Biophysics, 424 (2004) 141-153.

Dubey et al., "Microencapsulation Technology and Applications", Defence Science Journal, 59 (1), 82-95 (2009).

Gan et al., "Role of NADPH-Cytochrome P450 Reductase and Cytochrome-b-$_5$/NADH-b$_5$ Reductase in Variability of CYP3A Activity in Human Liver Microsomes", Drug Metabolism and Disposition, 37 (1), 90-96 (2009).

Hallenbeck, P.C. and Benemann, John R., "Biological hydrogen production: fundamentals and limiting processes", International Journal of Hydrogen Energy, 27 (11-12), 1185-1193 (2002).

Hasemann et al., "Structure and function of cytochromes P450: a comparative analysis of three crystal structures", Structures, 3 (1), 41-62 (1995).

Kapdan et al., "Bio-hydrogen production from waste materials", Enzyme and Microbial Technology, 38 (2006) 569-582.

Kurkin et al., "The membrane-bound [NiFe]-hydrogenase (Ech) from *Methanosarcina barkeri*; unusual properties of the iron-sulphur clusters", Eur. J. Biochem., 269, 6101-6111 (2002).

Long et al., "Characterization of a HoxEFUYH type of [NiFe] hydrogenase from *Allochromatium vinosum* and some EPR and IR properties of the hydrogenase module", J. Biol. Inorg. Chem., 12, 62-78 (2007).

McIntosh et al., "The [NiFe]-Hydrogenase of the Cyanobacterium *Synechocystis* sp. PCC 6803 Works Bidirectionally with a Bias to H$_2$ Production", Journal of the American Chemical Society, 133, 11308-11319 (2011).

McTernan et al., "Intact Functional Fourteen-subunit Respiratory Membrane-bound [NiFe]-Hydrogenase Complex of the Hyperthermophilic Archaeon *Pyrococcus furiosus*", The Journal of Biological Chemistry, 289 (28) 19364-19372 (2014).

McTernan et al., "Intact Functional Fourteen-subunit Respiratory Membrane-bound [NiFe]-Hydrogenase Complex of the Hyperthermophilic Archaeon *Pyrococcus furiosus*", Supplementary Material, 8 pages.

Meuer et al., "Purification and catalytic properties of ECH hydrogenase from *Methanosarcina barkeri*", Eur. J. Biochem., 265, 325-335 (1999).

Rakhely et al., "Cyanobacterial-Type, Heteropentameric, NAD+-Reducing NiFe Hydrogenase in the Purple Sulfur Photosynthetic Bacterium *Thiocapsa roseopersicina*", Applied and Environmental Microbiology, 70 (2), 722-728 (2004).

Schmitz et al., "HoxE-a subunit specific for the pentameric bidirectional hydrogenase complex (HoxEFUYH) of cyanobacteria", Biochimica et Biophysica Acta, 1554, 66-74 (2002).

Soboh et al., "Purification and catalytic properties of a CO-oxidizing: H2-evolving enzyme complex from *Carboxydothermus hydrogenoformans*" Eur. J. Biochem., 269, 5712-5721 (2002).

Soboh et al., "A multisubunit membrane-bound [NiFe] hydrogenase and an NADH-dependent Fe-only hydrogenase in the fermenting bacterium *Thermoanaerobacter tengcongenis*", Microbiology, 150, 2451-2463 (2004).

Wikipedia—Bacteriorhodopsin (Downloaded from the internet on Jun. 22, 2015). 2 pages total.

Zhanhua et al., "Protein subunit interfaces: heterodimers versus homodimers", Bioinformation, 1 (2); 28-39 (2005).

Sligar S. "The self-assembly of integral membrane proteins into Nanodiscs" Sligar Lab, University of Illinois at Urbana-Champaign. Printout website dated Jun. 13, 2010, http://sligarlab.life.uiuc.edu/nanodisc/overview.html.

International Search Report issued for PCT Application No. PCT/US2015/051516 filed on Sep. 22, 2015 in the name of Lawrence Livermore National Security, LLC. Mail Date: Jan. 25, 2016.

Written Opinion issued for PCT Application No. PCT/US2015/051516 filed on Sep. 22, 2015 in the name of Lawrence Livermore National Security, LLC. Mail Date: Jan. 25, 2016.

International Search Report issued for PCT Application No. PCT/US2015/051172 filed on Sep. 6, 2016 in the name of Lawrence Livermore National Security, LLC. Mail Date: Dec. 13, 2016.

Written Opinion issued for PCT Application No. PCT/US2015/051172 filed on Sep. 6, 2016 in the name of Lawrence Livermore National Security, LLC. Mail Date: Dec. 13, 2016.

\* cited by examiner

NANOLIPOPROTEIN PARTICLES COMPRISING HYDROGENASES AND RELATED PRODUCTS, METHODS AND SYSTEMS

CROSS REFERENCE TO RELATED APPLICATIONS

This application claims priority to U.S. Provisional Application entitled "Functional membrane protein capture, solubilization, and purification from native cell membrane fractions using nanolipoprotein particles formed in situ" Ser. No. 61/020,638, filed on Jan. 11, 2008 and to U.S. Provisional Application entitles "Hydrogen Production by Membrane Associated Hydrogenases in Soluble Nanolipoprotein Particles" Ser. No. 61/115,446, filed on Nov. 17, 2008, the disclosure of each of which is incorporated herein by reference in its entirety. This application may also be related to U.S. patent application entitled "Methods and Systems for Monitoring Production of a Target Protein in a Nanolipoprotein Particle" Ser. No. 12/118,530, filed on May 9, 2008, to U.S. patent application entitled "Methods and Systems for Producing Nanolipoprotein Particle" Ser. No. 12/118,396, filed on May 9, 2008 and to U.S. application entitled "Nanolipoprotein Particles and Related Methods and Systems for Protein Capture Solubilization and/or Purification" filed on the same day of the present Application with Ser. No. 12/352,548, the disclosure of each of which is incorporated herein by reference in its entirety.

STATEMENT OF GOVERNMENT GRANT

The U.S. Government has rights in this invention pursuant to Contract No. Contract No. DE-AC52-07NA27344 between the U.S. Department of Energy and Lawrence Livermore National Security, LLC.

FIELD

The present disclosure relates to nanolipoprotein particles (NLPs) and in particular to NLPs including as a target protein a membrane associated protein that is a biocatalyst and more particularly a hydrogenase.

BACKGROUND

Membrane-associated proteins and protein complexes account for ~30% or more of the cellular proteins. Membrane proteins are held within a bilayer structure. The basic membrane bilayer construct consists of two opposing layers of amphiphilic molecules know as phospholipids; each molecule has a hydrophilic moiety, i.e., a polar phosphate group/derivative, and a hydrophobic moiety, i.e., a long hydrocarbon chain. These molecules self-assemble in a biological (largely aqueous) environment according to thermodynamics associated with water exclusion or hydrophobic association.

Some membrane associated proteins are also biocatalysts, i.e. biological compounds able to affect the rate of a chemical reaction, such as transformations involving organic compounds.

In particular, certain membrane proteins play a key role in the transport of energy across cellular boundaries. Recently, several membrane proteins have been identified as attractive candidates for enabling the conversion of biomass and/or solar energy to renewable fuels. Among these enzymes are hydrogenases, which can function to catalyze the production of molecular hydrogen from protons.

Constructions of ex vivo and/or in vitro biocatalytic systems including hydrogenase is often challenging in view of the need to reproduce the conditions necessary to provide the enzyme in an active form and in view of the instability to oxygen and sensitivity to byproducts that characterize several of those biocatalysts.

SUMMARY

Provided herein are products, methods and systems that are based on a membrane bilayer mimetic in the form of a nanolipoprotein particle that includes a hydrogenase and allow, in several embodiments, performance in vitro of chemical reaction associated with the hydrogenase, such as hydrogen production.

According to a first aspect, a nanolipoprotein particle is disclosed. The nanolipoprotein particle comprises a target protein, a membrane forming lipid and a scaffold protein, wherein the target protein is a membrane associated hydrogenase.

According to a second aspect, a biocatalyst assembly is disclosed. The biocatalyst assembly comprises a nanolipoprotein particle immobilized to a support, and the nanolipoprotein particle comprises a target protein, a membrane forming lipid and a scaffold protein. In the biocatalyst assembly, the target protein is a membrane associated hydrogenase.

According to a third aspect, a method to perform a chemical reaction catalyzed by a membrane associated hydrogenase is disclosed. The method comprises providing reagents for performing said chemical reaction, and providing a nanolipoprotein particle comprising the membrane associated hydrogenase, a membrane forming lipid and a scaffold protein. The method further comprises contacting the reagents with the nanolipoprotein particle for time and under conditions to allow the chemical reaction catalyzed by said membrane associated hydrogenase to occur.

According to a fourth aspect, a system to perform a chemical reaction catalyzed by a membrane associated hydrogenase is disclosed. The system comprises a nanolipoprotein particle and reagents for performing said chemical reaction. In the system, the nanolipoprotein particle comprises the membrane associated hydrogenase, a membrane forming lipid and a scaffold protein, and the nanolipoprotein particle and the reagents can be contacted for a time and under condition to allow the chemical reaction catalyzed by said membrane associated hydrogenase to occur.

According to a fifth aspect, a device for performing a chemical reaction associated to a membrane associated hydrogenase is disclosed. The device comprises a substrate compartment, and a hydrogenase compartment, with the substrate compartment in communication with the hydrogenase compartment. In the device, the hydrogenase compartment comprises a biocatalyst assembly, with the biocatalyst assembly comprising a nanolipoprotein particle immobilized to a support, and with the nanolipoprotein particle comprising a membrane associated hydrogenase capable of performing the chemical reaction, a membrane forming lipid and a scaffold protein. In the device, the substrate compartment is configured to comprise a substrate for the chemical reaction catalyzed by the membrane associated hydrogenase and to allow contact between said substrate and said membrane associated hydrogenase. A product compartment can also be included that is in communication with the hydrogenase compartment and is configured to comprise product produced following the reaction of the substrate with the membrane associated hydrogenase The products, methods and systems herein described, allow in several embodiments, performance of hydrogen production reactions with a catalytic turnover rate several orders of magnitude higher than corresponding inorganic catalysts.

The products, methods and systems herein described, further allow in several embodiments, to produce nearly theoretical yields of hydrogen from substrates, such as glucose or starch if compared with corresponding in vivo processes, in view of the elimination of competing cellular processes, such as, in case of hydrogenases, the processes which utilize hydrogen as an energy source.

The products, methods and systems herein described, further allow in several embodiments, to solubilize a membrane associated hydrogenase enzyme with very unique functionalities, such oxygen stability, preferential hydrogen producing activity, and/or thermal stability.

The products, methods and systems herein described, further allow to purify, and in particular, crudely purify, an entire hydrogenase enzyme complex in a functional form, and to enable subsequent mechanistic studies of the hydrogenase enzyme which require solubility.

The products, methods and systems herein described can be applied in several fields including basic biology research, applied biology, bio-engineering, bio-energy, and bio-fuels.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 7 shows a schematic representation of a hydrogen production device according to an embodiment herein disclosed. In particular, Panel a. shows a schematic illustration of a hydrogen production reaction according to an embodiment herein disclosed. Panel b. shows a schematic representation of a hydrogen production device wherein hydrogen is produced through the reaction of Panel a.

DETAILED DESCRIPTION

Figure 1:
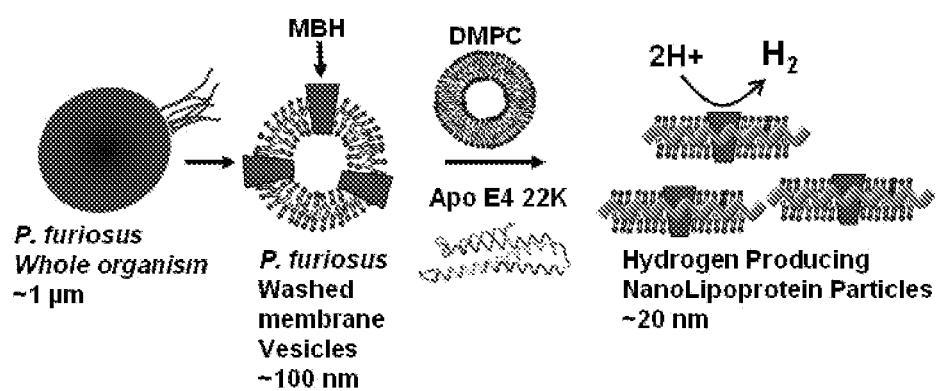
FIG. 1 shows a schematic illustration of a process to provide a MBH-NLP according to an embodiment herein disclosed.

Nanolipoprotein particles are herein disclosed that comprise a hydrogenase in its catalytically active form and related assemblies, devices, methods and systems.

The term "nanolipoprotein particle" "nanodisc" "rHDL" or "NLP" as used herein indicates a supramolecular complex formed by a membrane forming lipid and a scaffold protein, that following assembly in presence of a target protein also include the target protein. The scaffold protein and target protein constitute protein components of the NLP. The membrane forming lipid constitutes a lipid component of the NLP.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide.

As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "scaffold protein" as used herein indicates any protein that is capable of self assembly with an amphipatic lipid in an aqueous environment, organizing the amphipatic lipid into a bilayer, and include but are not limited to apolipoproteins, lipophorines, derivatives thereof (such as truncated and tandemly arrayed sequences) and fragments thereof (e.g. peptides), such as apolipoprotein E4, 22K fragment, liphorin III, apolipoprotein A-1, apolipophorin III from the silk moth *B. mori*, and the like. In particular, in some embodiments rationally designed amphipathic peptides can serve as a protein component of the NLP.

In some embodiment, the peptides are amphipatic helical peptides that mimic the alpha helices of an apolipoprotein component that are oriented with the long axis perpendicular to the fatty acyl chains of the amphipatic lipid and in particular of the phosphoplipid.

The term "target protein" or "membrane associated protein" as used herein indicates any protein having a structure that is suitable for attachment to or association with a biological membrane or biomembrane (i.e. an enclosing or separating amphipathic layer that acts as a barrier within or around a cell). In particular, target proteins include proteins that contain large regions or structural domains that are hydrophobic (the regions that are embedded in or bound to the membrane); those proteins can be extremely difficult to work with in aqueous systems, since when removed from their normal lipid bilayer environment those proteins tend to aggregate and become insoluble. Accordingly, target proteins are protein that typically can assume an active form wherein the target protein exhibits one or more functions or activities, and an inactive form wherein the target protein doe not exhibit those functions/activities. Exemplary target proteins include but are not limited to membrane proteins, i.e. proteins that can be attached to, or associated with the membrane of a cell or an organelle, such as integral membrane proteins (i.e. proteins (or assembly of proteins) that are permanently attached to the biological membrane.), or peripheral membrane proteins (i.e. proteins that adhere only temporarily to the biological membrane with which they are associated). Integral membrane proteins can be separated from the biological membranes only using detergents, non-polar solvents, or sometimes denaturing agents. Peripheral membrane proteins are proteins that attach to integral membrane proteins, or penetrate the peripheral regions of the lipid bilayer with an attachment that is reversible.

In the nanolipoprotein particles herein disclosed, at least one target protein of the NLP is a membrane associated hydrogenase. The wordings "membrane associated hydrogenase", "membrane bound hydrogenase" or "MBH" as used herein indicate a hydrogenase having a structure that is suitable for attachment to or association with a biological membrane or biomembrane. The term "hydrogenase" as disclosed herein indicates an enzyme that is capable of promoting formation and/or utilization of molecular hydrogen, and in particular is capable of catalyzing the conversion of protons to molecular hydrogen (herein also hydrogen production reaction), and/or the reverse reaction of converting molecular hydrogen to protons. Hydrogenases include enzymes classified according to the two transition metals coordinated at the active site (i.e. Ni and/or Fe), as [Ni/Fe] [Fe/Fe] and [Fe] wherein the [N/Fe] class include [Ni/Fe/Se] hydrogenases, i.e. [Ni/Fe] hydrogenase wherein one of the Ni-bound cysteine residues is replaced by selenocysteine. Membrane associated hydrogenases include several metalloenzymes which catalyze the reversible reduction of protons to hydrogen using organic matter and/or light as energy sources. Exemplary membrane associated hydrogenases include the H(2) uptake [Ni/Fe]hydrogenases which are membrane bound hydrogenase which perform respiratory hydrogen oxidation, and the membrane-associated, energy-converting, H(2) evolving hydrogenases which tend to have multiple subunits, (six or more) and function in vivo to dispose of excess reducing equivalents (by reducing protons) produced by the oxidation of organic compounds (see [22] and [23] incorporated herein by reference in their entirety).

More particularly, exemplary [Ni/Fe] hydrogenases that can be comprised in the MBH-NLP herein disclosed, with unique and attractive properties for bioenergy production are provided by [Ni/Fe/Se]-hydrogenase from *Desulfomicrobium baculatum*, [27] (which is oxygen tolerant), the MBH from *Allochromatium vinosum* (which has a very high rate of hydrogen oxidation, comparable to that of platinum). [2], the MBH from *Ralstonia* species has been shown to produce hydrogen in the presence of oxygen. [1] and a bidirectional heteromultimeric hydrogenases of *Klebsiella pneumoniae* able to bind soluble cofactors (see [22] for complete classification).

An additional example of [Ni/Fe] hydrogenase is the membrane hydrogenase of *Pyrococcus Furiosus* (PF-MBH). PF-MBH has ratio of $H_2$ evolution to $H_2$ oxidation activity of approximately 2,350. The enzyme operates optimally at 90 degrees C. in washed membranes. Purified PF-MBH contains 2 main subunits ($\alpha$ and $\beta$) in 1:1 ratio with a molecular mass of about 65 kDa. The protein contains about 1 Ni and 4 Fe atoms per mole, The a subunit contains the [Ni/Fe] active site. The open reading frames in the operon which encode the active site have sequence homology to MBH [Ni/Fe] complexes from *Methanosarcina barkeri*, *Escherichia coli*, and *Rhodospirillum rubrum* PF-MBH has ratio of $H_2$ evolution to $H_2$ oxidation activity of approximately 2,350. The enzyme operates optimally at 90 degrees C. in washed membranes. (which in certain embodiments could be an advantage in terms of thermal stability) [12].

A skilled person is be able to identify additional membrane associated hydrogenases suitable to be included in the nanolipoprotein particles herein described upon reading of the present disclosure.

In the nanolipoprotein particles herein disclosed the membrane associated hydrogenase is comprised in a functional or active form, i.e. performing or able to perform, under appropriate conditions, one or more of the functions associated to the MBH in a system, such as an organism, from which the hydrogenase has been derived.

The term "membrane forming lipid" or "amphipatic lipid" as used herein indicates a lipid possessing both hydrophilic and hydrophobic properties that in an aqueous environment assemble in a lipid bilayer structure that consists of two opposing layers of amphipathic molecules know as polar lipids. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols and alkylphosphocholins. Amphipatic lipids include but are not limited to membrane lipids, i.e. amphipatic lipids that are constituents of a biological membrane, such as phospholipids like dimyristoylphosphatidylcholine (DMPC) or Dioleoylphosphoethanolamine (DOPE) or dioleoylphosphatidylcholine (DOPC), or dipalmitoylphosphatidylcholine (DPPC). Additional exemplary polar lipids include synthetic phospholipid-based asymmetric bolaamphiphile mimetic of the natural lipids in archae. (Sun, X. et al 2006), which are particularly suitable in embodiments wherein performance of reactions at a high temperature is desired since the structure of the archaea lipids is thought to keep the membrane intact at upwards of 90° C. (see also [23]).

The membrane forming lipid and the protein components of the NLP are generally able to self-assemble in a biological (largely aqueous) environment according to the thermodynamics associated with water exclusion (increasing entropy) during hydrophobic association.

In some embodiments of the methods and systems herein provided, the amphipatic lipid and the protein components of the NLP are allowed to assembly in a cell free expression system.

In particular, the NLP components can be contacted to form an admixture that is then preferably subjected to a temperature transition cycle in presence of a detergent. In the temperature cycle, the temperature of the admixture is raised above and below the gel crystalline transition temperature of the membrane forming lipids. Exemplary procedures are illustrated in Example 1 and 4 of the present application and comprise in situ incorporation of hydrogenase into self-assembling NLPs (described in examples section where lipid, scaffold, MBH, possibly surfactant are added together and subjected to transition temp fluctuation to assemble NLPs and incorporate MBH simultaneously A further description of this method can also be found in the U.S. patent application entitled "Nanolipoprotein Particles and Related Methods and Systems for Protein Capture Solubilization and/or Purification" filed on the same day of the present application with Ser. No. 12/352,548 and incorporated herein by reference in its entirety. Additionally the MBH-NLPs herein disclosed are also expected to be provided by incubation of pre-formed NLPs with MBH and possibly surfactant, and the "one pot" synthesis, where gene sequences encoding the MBH and scaffold protein are used to direct the (cell-free) synthesis of the necessary NLP components in "one pot" extensively described in U.S. patent application entitled "Methods and Systems for Producing Nanolipoprotein Particle" Ser. No. 12/118,396, filed on May 9, 2008 herein incorporated by reference in its entirety. The MBH may be supplied in the following forms in the above variants: inside the native membrane, purified from the native membrane, in natural or artificial liposomes. The MBH may also be expressed recombinantely in another organism such as E. Coli, and be used in the recombinant form in the native membrane, liposomes, or purified.

Assembly of MBH-NLPs can be detected using techniques identifiable by the skilled person upon reading of the present disclosure that include Atomic Force Microscopy or Transmission Electron Microscopy. The insertion of MBH in NLPs can be inferred from a comparison of size between empty NLP and supposed MBH NLP using: Size Exclusion Chromatography, Native and denaturing Poly-Acrylamide Gel Electrophoresis, and a height comparison in AFM. An exemplary use of some of these techniques is illustrated in the Examples section shown in FIGS. 2, 3, 4 and 6.

The term "detect" or "detection" as used herein indicates the determination of the existence, presence or fact of an MBH, MBH-NLP and/or related activities in a limited portion of space, including but not limited to a sample, a reaction mixture, a molecular complex and a substrate. A detection is "quantitative" when it refers, relates to, or involves the measurement of quantity or amount of the MBH, MBH-NLP and/or related activities (also referred as quantitation), which includes but is not limited to any analysis designed to determine the amounts or proportions of the MBH, MBH-NLP and/or related activities. A detection is "qualitative" when it refers, relates to, or involves identification of a quality or kind of the MBH, MBH-NLP and/or related activities in terms of relative abundance to another MBH, MBH-NLP and/or related activities, which is not quantified.

The assembled MBH-NLPs include the MBH in a functional or active form and in particular the MBH active site may either be in a reduced or oxidized state.

In several embodiments, an MBH-NLP can contain a mass ratio of between 1:1 and 20:1 of lipid to scaffold protein. The ratio of scaffold protein to MBH can be varied from 1:0.025 to 1:1. The concentration of membrane forming lipid can be varied from 0.1 to 20 mg/per mL. A skilled person will be able to identify the appropriate ratios based on the size and dimension (lipid to scaffold protein ratio) and the protein-protein interactions (Scaffold protein to MBH ratio) characterizing the MBH of choice.

Functionality of the MBH comprised in the NLP can be detected by several techniques that are based on the detection of performance of ay reaction that is associated to a functional MBH of interest. Exemplary techniques to detect hydrogenase activity include detection of hydrogen production catalyzed by an MBH-NLP and detection of conversion of molecular hydrogen to protons catalyzed by the MBH-NLP. Hydrogen production can be in particular quantitatively or qualitatively detected by measuring $H_2$ evolution in a gas chromatograph after incubating the MBH-NLP with a suitable electron donor, such as reduced methyl viologen, reduced benzyl viologen, reduced ferredoxin or NADPH, in a buffered aqueous solution, that can be anaerobic. [12] Hydrogen oxidation activity can be detected, for example by a spectrophotometric assay performed by monitoring, for example, the absorbance change of benzyl viologen or methyl viologen incubated with hydrogenase at 578 nm [11]. Additional techniques to detect hydrogenase activity are identifiable by a skilled person upon reading of the present disclosure.

In several embodiments, the hydrogenase activity detected for MBH-NLPs is expected to be comparable with the activity of the hydrogenase in the crude MBH. In particular in some embodiments the hydrogenase activity can include a range of activities between ~7.5 nmol hydrogen produced per min per mg protein and ~600 umol hydrogen produced per min per mg protein. (see also [23] incorporated herein by reference in its entirety).

In several embodiments, hydrogenases comprised in MBH-NLP have catalytic turnover rates several orders of magnitude higher than advanced inorganic catalysts [7], eliminate competing cellular processes which utilize hydrogen as an energy source, and allow ex-vivo solution-phase synthetic enzymatic reactions that have been shown to produce nearly theoretical yields of hydrogen from glucose or starch. [6, 8, 9]

In several embodiments, the MBH-NPL herein described can be used in method to perform a chemical reaction catalyzed by the MBH, and in particular, in embodiments where the MBH is a metalloenzyme derived from an organism, to perform in vitro a chemical reaction that can be performed by the hydrogenase in the organism.

The wording "chemical reaction" as used herein indicates any reaction associated to a membrane associated hydrogenase, which include but are not limited to the reduction of protons to form hydrogen gas (hydrogen production) or the oxidation of hydrogen to form protons.

The terms "catalyzed", "catalyze" and "catalysis" as used herein relates to the process in which the rate of a chemical reaction is increased by means of a chemical substance known as a catalyst, which in the present application, is a hydrogenase and in particular a membrane bound hydrogenase.

The wording "in vitro", as used herein, indicates a technique of performing a given procedure in a controlled environment outside of a living organism and includes any procedures experimentations or measurements done in an artificial environment outside the living organism comprising the procedures commonly identified as "ex vivo", The term "organism" and in particular "living organism" as used herein indicates an individual biological system capable to carry on the activities associated with life, which includes but is not limited to animal, plant, fungus, or micro-organisms. In at least some form, organisms are capable of reacting to stimuli, reproduction, growth and maintenance as a stable whole. An organism may be unicellular or multicellular, which include organisms, such humans, constituted by many billions of cells grouped into specialized tissues and organs. Exemplary living organisms for the MBH-NLPs of the present disclosure include but are not limited to several prokaryotes such as *Allochromatium vinosum, Methanosarcina barkeri, Escherichia coli*, and *Rhodospirillum rubrum Desulfomicrobium baculatum, Ralstonia* species and *Pyrococcus furiosus, C. hydrogenoformans, R. rubrum, Rubrivax gelatinosus, Methanothermobacter thermoautotrophicus, Methanothermobacter marburgensis, Thermoanaerobacter tengcongensis*. [Ref. 21] Additionally: organisms listed in Table 1 of [Ref 22] as containing hydrogenase in groups 1 and 4.

Living organisms perform several chemical reactions in the sense of the present disclosure, including but not limited to hydrogen production and hydrogen oxidation, where hydrogen oxidation can be coupled to the reduction of electron acceptors such as oxygen, nitrate, sulfate, carbon dioxide, and fumarate.

In some embodiments, the chemical reaction catalyzed by the MBH-NLP is hydrogen production, and the NLPs incorporated with MBH can be used to catalyze production of hydrogen starting from an organic substrate, that is processed to provide protons that are then converted to molecular hydrogen by the MBH-NLPs.

In particular, the protons can be present in any aqueous medium and be provided to the MBH via electron donors also present in the reaction mixture [6, 8, 11 and 12]. In particular any electron donor of a suitable electrochemical potential energy and accessibility required to reduce the active site of the MBH can be used to provide the protons to the MBH and include but are not limited to NADPH, NADH, cytochromes, coenzyme F20 and reduced viologen.

In certain embodiments wherein the reaction is performed as a solution phase reactions, MBH-NLPs may be advantageous to MBH in crude membrane because they may be used at higher concentrations and also may provide better access to other soluble electron donors/cofactors than MBH in crude membranes, which under certain conditions could out of the solution. MBH in NLPs is also advantageous compared with purified MBH, because purified membrane proteins often require surfactants to remain soluble and in functional form. The presence of surfactants may hinder other aspects of the hydrogen production reaction. MBH-NLPs may be preferable to MBH in the native membrane immobilized on solid supports, because the nanoscale dimensions of the NLPs enable a higher packing density of the MBH. Additionally, the MBH-NLPs can be attached to the support (through the apolipoprotein) in such a way as to provide access to both sides of the lipid bilayer, providing increased access of the reactants to the active site of the hydrogenase.

In several embodiments, hydrogen production can be optimized by varying the temperature of the reaction vessel between about 25 degrees C. and about 95 degrees C. depending on the optimal turnover rate for the type of MBH used. Additionally, variables such as mass transport, solution pH, ionic strength, hydrogenase concentration, cofactor and/or electron donor and/or reducing agent concentration, oxygen content reduced, and hydrogen content can be optimized.

In some embodiments, hydrogen production can be performed by hydrogenases that preferentially catalyze the reaction under appropriate conditions.

In some embodiments, hydrogen production can be performed by MBH-NLPs herein disclosed wherein the MBH is a [Fe/Fe] hydrogenases. In those embodiments, the reaction condition are based on the characteristics of the [Fe/Fe] MBH which generally promote hydrogen production, as opposed to the reverse reaction, hydrogen oxidation to protons, and in general are extremely oxygen sensitive. Fe/Fe MBH is extremely rare, therefore, no H2 production by Fe/Fe MBH has been observed (to the Applicants' knowledge). The existence of a membrane bound Fe/Fe hydrogenase has been inferred from the gene sequence of *Eubacterium Acidaminophilum*. [25]. Applicants however expect that the same conditions required for H2 production from [Ni/Fe] hydrogenases would also be appropriate for [Fe/Fe] hydrogenases. In those embodiments however, particular attention must be placed on maintaining the Fe/Fe in an anaerobic and reducing environment.

In some embodiments, hydrogen production can be performed by MBH-NLPs herein disclosed wherein the MBH is a [Ni/Fe] hydrogenase. In those embodiments, the reaction condition are based on the characteristics of the [Ni/Fe] hydrogenases which are more stable to oxygen exposure compared to those with [Fe/Fe] active sites, but depending on the reaction condition can preferentially catalyze proton production from hydrogen.

In particular, in some embodiments, the [Ni/Fe] MBH, is an MBH from the extremophile *P. Furiosus* (PF-MBH). In those embodiments, the reaction condition are based on the characteristics of the PF-MBH which can be used for in vitro hydrogen production and has the advantage of a greater oxygen resistance when compared to other [Ni/Fe] types of hydrogenase, together with a greater propensity for catalyzing hydrogen production than other known [Ni/Fe] type hydrogenases. Additionally, PF-MBH can be exposed to oxygen (e.g. in air) for a certain amount of time and then treated with reducing agent or excess hydrogen for reverting any possible oxidation of the active site.

Exemplary reactions for hydrogen production are exemplified in the example section with reference to MBH from *Pyrococcus furiosus* (PF-MBH). A skilled person will be able to identify any appropriate or necessary variations of the procedures described in details in the example section to perform hydrogen production using MBH-NLPs other than PF-MBH-NLPs.

Hydrogen production can be detected as indicated herein and in particular additionally using commercially available hydrogen sensors such as that described in the html_page_mstc/technologies/microsensors/hydrogensensor of the website sandia.gov.

In some embodiments, the chemical reaction catalyzed by the MBH-NLP is oxidation of molecular hydrogen, and the NLPs incorporated with MBH can be used to catalyze conversion of hydrogen gas to generate electricity.

In particular, in several embodiments, hydrogen can be supplied as a gas, either in pure form or in a carrier gas such as air or nitrogen. The hydrogen is introduced to the enzyme by bubbling into the solution containing the enzyme [26]. The hydrogen oxidation reaction can be optimized by choice of electrode material, pH, ionic strength, concentration of hydrogen gas, physical orientation of MBH-NLP on electrode (optimized for fast electron transfer), buffering system, and mass transport.

A skilled person will be able to identify the above procedures and any appropriate or necessary variations upon reading of the present disclosure and in particular of the detailed description and the examples section.

In some embodiments, hydrogen oxidation can be performed by hydrogenases that preferentially catalyze the reaction under appropriate conditions. Higher concentrations of hydrogen in air or inert gas will facilitate the oxidation as opposed to the hydrogen production reaction.

In several embodiments of the present disclosure, reagents for the performance and/or detection of a chemical reaction catalyzed by MBH-NLPs herein disclosed, and in can be provided in systems for performing the chemical reaction, also including the appropriate MBH-NLP.

In particular, in some embodiments the MBH may be supplied in the following forms in the above variants: inside the native membrane, purified from the native membrane, in natural or artificial liposomes. The MBH may also be expressed recombinantely in another organism such as *E. Coli*, and be used in the recombinant form in the native membrane, liposomes, or purified.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (i.e. wash buffers and the like).

In some embodiments, nanolipoprotein particles MBH-NLPs provide a well defined water-soluble matrix that maintains the enzymatic activity and that is amenable to incorporation into more complex architectures.

Exemplary architectures comprise a biocatalyst assembly suitable for performing one or more reaction catalyzed by the hydrogenase, wherein the MBH-NLPs herein described is immobilized to a suitable support or scaffold.

The term "support" as used herein indicates any material or substance suitable to hold up or serve as a foundation or prop for the MBH-NLPs herein described.

In some embodiments, a support for MBH-NLP comprises a material for attaching the MBH-NLPs to a solid phase so that the MBH-NLPs can be isolated from the liquid phase which can then be removed and replenished. (See Example 6) This type is most useful for hydrogen production reactions. These supports need to be thermally and chemically stable, (i.e. at temperatures of up to 95 degrees C. and acidic pH) but not necessarily conductive. The chemical stability is required because it is likely that the surface of the support will be modified for chemical attachment of the MBH-NLPs. Materials which satisfy these criteria are silicon, glass ($SiO_2$), and carbon (i.e. glassy carbon, diamond). The morphology of the material (esp. in the case of $SiO_2$) can be designed to have a high surface area in order to provide a high number of MBH active sites in a given volume and mass of assembly. This type of support is likely advantageous to the hydrogen production and storage device described in Example 7.

In some embodiments, a support for MBH-NLP comprises a material suitable to conduct electrons extracted from hydrogen gas. These electrodes can be made of a chemically stable, electrically conductive material such as glassy carbon, highly oriented pyrolytic graphite, carbon nanotubes, or carbon nanofibers. The latter will provide a higher surface area to maximize surface area of hydrogenase.

The term "immobilize" as used herein indicates the act or the condition of reducing up to minimizing or eliminating the motion of a MBH-NLP. In particular, in some embodiments, the MBH-NLP can be immobilized via a chemical linkage to the NLP lipid or a chemical linkage through the apolipoprotein. The chemical linkage through the lipid can be provided, for example, using a biotin labeled lipid and attaching the protein avidin to the surface of the support. Additionally, the NLP can be attached through the apolipoprotein using a histidine tag on the protein and attaching to a Nickel-NTA terminated support. The latter is described in detail in [15]. The NLP can also be attached through other chemical linkages from the apolipoprotein, for example, through lysine residues an amide bond can be formed between the apolipoprotein and a support functionalized with carboxylic acid groups.

In some embodiments, the MBH-NLPs could also be immobilized to solid supports for heterogeneous catalysis, which would provide the opportunity to flush reaction byproducts which could poison hydrogenase activity, and/or provide the opportunity to regenerate the catalyst using reducing agents that can then be easily removed. In particular in some embodiments, the MBH-NLP can be immobilized to a support configured to enable, and in particular optimized hydrogen production.

In some embodiments, the MBH-NLPs could be immobilized on electrically conductive supports and contain a type of hydrogenase which preferentially oxidizes hydrogen. In some of those embodiments, introduction of hydrogen can be used to drive an electrical current which is collected at the electrode. The MBH-NLPs are immobilized on the anode and the cathode is modified with an electrocatalyst which uses the protons generated from the hydrogen oxidation to reduce oxygen. If the MBH used is oxygen sensitive, two chambers (each containing one anode and one cathode) must be separated by a proton conductive membrane. Alternatively, oxygen-insensitive MBHs can also be used without a proton conductive membrane. Such devices with MBH (not in NLPs) have been described in reference [26].

In some embodiments, the MBH-NLPs herein disclosed and/or related assemblies, can be used for a modular H2 production that is expected to allow interfacing with storage capability. In this case, all necessary reagents required to supply energy (i.e. biomass, cellulose, starch, glucose, etc.) are incorporated with the necessary enzymes (for example, glucose dehydrogenase, NADPH, and ferredoxin NADPH oxidoreductase) to utilize and transfer that energy to an electron donor (e.g. ferredoxin) which can reduce the hydrogenase-MBH active site. The reduced hydrogenase can then produce hydrogen gas from the aqueous solution. The gas that is generated is collected and stored in a material optimized for hydrogen storage, such as metal-doped carbon aerogels.

In some embodiments, the MBH-NLPs herein disclosed and/or related assemblies, allows improvements of an ex vivo enzymatic strategy, in particular when oxygen stable, active hydrogenases and other enzymes involved in conversion of biomass to hydrogen can be immobilized on surfaces for reactant cycling and to prevent catalyst poisoning from reaction byproducts.

In some embodiments, the MBH-NLPs herein disclosed and/or related assemblies allow solubilization of MBH is retained in a synthetic membrane in NLPs, so that the MBH retains activity in the presence of oxygen for a significantly longer time period than when the MBH is removed from the membrane entirely.

In some embodiments, MBH-NLPs herein described are expected to find application in a linked network of chemical processes that produces hydrogen through fossil fuel reforming, biomass conversion, and electrolytic, biophotolytic, or thermochemical splitting of water; stores hydrogen chemically or physically: and converts the stored hydrogen to electrical energy and heat at the point of use.

In some embodiments, MBH-NLPs herein described have at least potential ability to enable commercially viable production of hydrogen from renewable resources, such as plant biomass. Hydrogen is a high energy density, potentially zero pollution transportation fuel and is therefore an extremely attractive candidate fuel for a future carbon neutral transportation system if it can be produced using renewable resources. Standard inorganic catalysts for conversion of biomass to hydrogen have low selectivities, require extremely high temperatures, are not abundant enough to satisfy a global need, and can be costly.

Additional uses and embodiments of the MBH-NLPs herein disclosed are based on the ability of the MBH-NLP to allow attachment of a functional membrane-bound biocatalyst to a solid support using the surrounding NLP as an attachment point, ability of the MBH-NLP to allow solubilization of a hydrogenase enzyme with very unique functionality (i.e. oxygen stability, preferential hydrogen producing activity, and thermal stability), a means for (crudely) purifying the entire enzyme complex in functional form, and enabling subsequent mechanistic studies of the hydrogenase enzyme which require solubility.

Exemplary architectures include devices, such as biomimetic hydrogen production devices, for performing one or more reactions catalyzed by the MBH-NLP of interest. An example of such a device is illustrated in Example 7 and FIG. 7b, wherein a hybrid microbial fuel cell is schematically illustrated (methods for extracting energy from the stored hydrogen are not depicted in the illustration). Additional devices can include a "hybrid self-contained biohydrogen production and storage device".

In several embodiments, such as the embodiments of Example 7, the device includes a product compartment. In other embodiments, products, hydrogen gas can separate itself by (e.g. bubbling out of the solution) or continually removed by flowing a carrier gas, such as nitrogen over the reaction vessel into a containment vessel. In particular, in certain embodiments the product compartment can be made of a nanofoam material that could be used to retain the product (H2 in hydrogen production). In some embodiments, once fully charged the nanofoam compartment could be removed, hydrogen released and combusted to heat water, produce steam and turn a turbine.

Further details concerning the nanoparticles, assemblies, devices, methods and systems herein disclosed, can be identified by the person skilled in the art upon reading of the present disclosure.

EXAMPLES

The methods and system herein disclosed are further illustrated in the following examples, which are provided by way of illustration and are not intended to be limiting.

In particular, in the following examples, a further description of the nanoparticles methods and systems of the present disclosure is provided with reference to applications wherein the membrane associated hydrogenases is the membrane hydrogenase of P Furiosus (PF-MBH). A person skilled in the art will appreciate the applicability of the features described in detail for nanoparticles comprising membrane associated hydrogenase from P Furiosus to nanoparticles including other membrane associated hydrogenases as defined herein. In particular, the examples of nanoparticles methods and systems herein provided although related to hydrogen production through nanolipoprotein particles comprising membrane associated hydrogenases also provide guidance to a skilled person to obtain nanolipoprotein particles able to catalyze other chemical reactions as defined herein.

In particular, the following examples described production and uses of MBH-NLPs including PF-MBH.

PF-MBH is the more oxygen resistant [Ni/Fe] type of hydrogenase, yet has a 2000-fold greater propensity for catalyzing hydrogen production compared to the reverse reaction. Importantly, the PF-MBH retains a significant fraction of initial activity in air over several days, and eventual oxidation of the active site can be reversed using reducing agents or excess hydrogen. For these reasons, the MBH from *P. Furiosus* is an extremely attractive candidate for bioenergy applications. However, the hydrogenase is associated with the water insoluble *P. furiosus* cell membrane, and several practical challenges, including solubilization of the enzyme while maintaining activity, must be overcome to enable the use of MBH either in the solution phase or immobilized on surfaces for heterogeneous catalysis.

Incorporating MBH into nanolipoprotein particles (NLPs) offers a potential solution to the problems associated with manipulating and utilizing MBH in crude membrane preparations. Here, we report the first successful biocatalysis by a bioenergy related membrane protein incorporated into NLPs. Synthesis of NLPs in the presence of MBH-containing *P. Furiosus* membranes enabled incorporation of the MBH into the NLPs, and thus solubilization of the active MBH in aqueous solution.

Example 1: Preparation of MBH-NLPs

Nanolipoprotein particles comprising membrane associate hydrogenases according to the approach schematically illustrated in FIG. 1.

In particular, FIG. 1 provides an overview of the process used to assemble MBH-NLPs: *P. furiosus* cells were first lysed and cellular membranes were separated and washed using centrifugation, forming insoluble membrane fragments and vesicles.

More particularly, preparation of washed membranes from *Pyroccocus furiosus* was performed as follows.

*P. furiosus*(DSM 3638) was grown in a 600 liter fermenter at 90 "C as previously described." Fifty grains of *P. furiosus* cells were osmotically lysed in 50 mM Tris, 2 mM sodium dithionite (DT), pH 8 and centrifuged at 50,000×g for 45 minutes. The resulting pellet was resuspended in the same buffer, and centrifuged in this manner an additional two times, and brought to a final resuspended volume with 5 mL of the same buffer. The sample was then anaerobically frozen in liquid nitrogen and sealed under argon.

A suspension of the membrane fragments was added to synthetic phospholipid 1,2-Dimyristoyl-sn-Glycero-3-Phosphocholine (DMPC), Apo E422k and cholate, a surfactant, using a cholate concentration above the critical micelle concentration (20 mM) in presence of a scaffold protein. The scaffold protein used was a truncated helical amphiphilic apoliprotein E with a mass of 22 kD (Apo E422k).

The phospholipid 1,2-Dimyristoyl-sn-Glycero-3-Phosphocholine (DMPC) was purchased from Avanti Polar Lipids, Inc. Sodium cholate and sodium DT were used as received from Sigma-Aldrich. The scaffold protein Apo E4 22K was produced according to published procedures. '7 Tris-Buffered Saline (TBS) was composed of 10 mM Tris, 0.15 M NaCl, 0.25 mM EDTA, and 0.005% Sodium Azide, pH 7.4. All solutions used were degassed and maintained under a positive pressure of argon prior to use.

The components were thermally cycled above and below the transition temperature of DMPC, followed by removal of excess DMPC and cholate by dialysis against buffer.

The NLPs were then separated from unincorporated proteins and lipids and were ready to be tested for hydrogen production.

Example 2: Identification and Characterization of MBH/NLPs: Size Exclusion Chromatography MBH/NLPs were produced according to a procedure exemplified in example 1. The particles were then separated from unincorporated free proteins and lipids using size exclusion chromatography (SEC)

Native and denaturing polyacrylamide gel electrophoresis of the SEC fractions was carried out according to published procedures. [16, 17]

Figure 2:
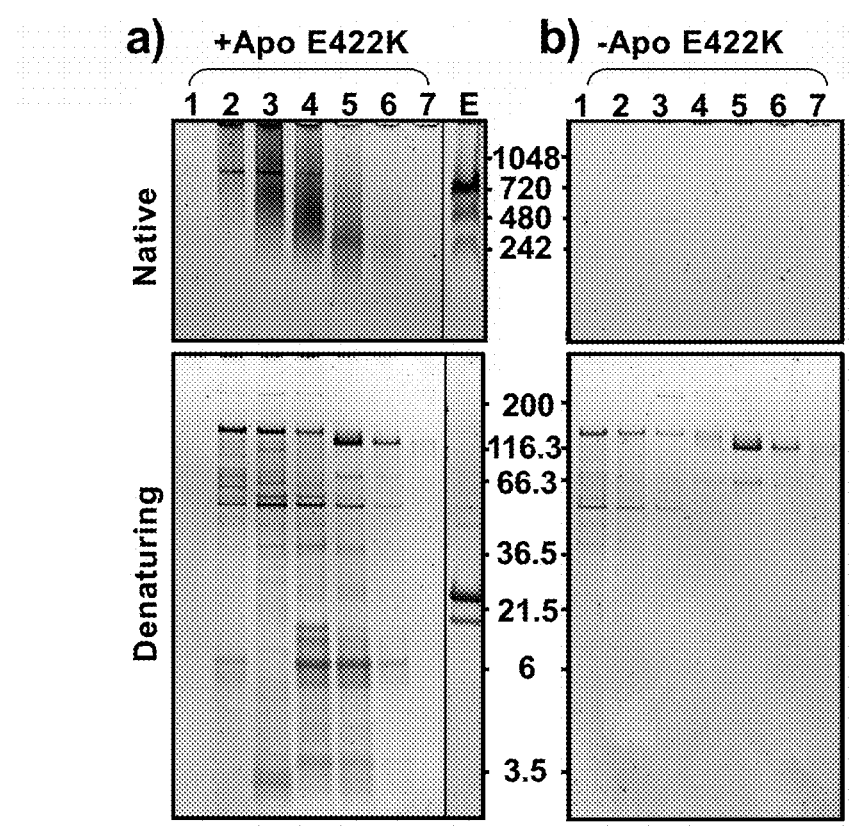
FIG. 2 shows identification of MBH-NLPs according to an embodiment herein disclosed. In particular, Panel a) shows exemplary native (top) and denaturing (bottom) polyacrylamide gel electrophoresis of sequential fractions collected after size-exclusion chromatography (SEC) of an Assembly A formed by NLP and a hydrogenase (+scaffold protein). The lane marked E corresponds to an unpurified "empty" NLP assembly. The bands in lanes 2-5 in the native gel in Panel a) are characteristic of NLP bands, both according to the molecular weight standards on the gel, as well as the SEC elution time. Panel b) shows exemplary native (top) and denaturing (bottom) polyacrylamide gel electrophoresis of sequential fractions collected after size-exclusion chromatography (SEC) of an Assembly B formed by a control formed by membrane lipids and a hydrogenase (−scaffold protein). The native gel in b) contains no NLP hands, consistent with the absence of scaffold protein in the assembly mixture

The results illustrated in FIG. 2 show representative native and denaturing polyacrylamide electrophoresis gels loaded with three assemblies. Assembly "A" contained all components required for incorporation of MBH into NLPs: lipid, surfactant, Apo E 422k, and MBH-containing membranes. Assembly "B" excluded the structure-directing scaffold protein, Apo E422k, from the assembly mixture and therefore served to elucidate the effects of NLP incorporation on MBH solubility, particle size, and hydrogenase activity.

Assembly "E" contained "empty" NLPs, which were prepared in the absence of MBH-containing membranes for comparison of particle size distributions to those present in MBH-NLPs.

FIG. 2a shows both native (top) and denaturing (bottom) polyacrylamide gels loaded with samples from SEC fractions resulting from MBH-NLP assembly A. Lanes 1-7 are from 1 mL SEC fractions collected at a flow rate of 0.5 tnL11ninute. Fraction collection began 15 minutes after injection (lane I).

The void volume of the column was 8 mL (16 minutes) using blue dextran as the marker. The broad smears in lanes 2-5 of the native gels are characteristic of NLP complexes. However, fractions 2, 3 and 4 appear to contain particles of larger size than the empty NLPs in Lane "E, consistent with a population of NLPs with *P. furiosus* membrane proteins incorporated into the particles. The corresponding denaturing SDS gel lanes (FIG. 2a bottom) show bands consistent with *P furiosus* membrane proteins, indicating incorporation of *P. furiosus* membrane proteins, including those that contribute to hydrogenase activity, into the NLP-like particles.

FIG. 2b shows SEC purification fractions of assembly B, where lanes 1-7 represent the same elution times as those in lanes 1-7 in FIG. 2a. The native gel contained only very low intensity bands in fractions 1, 2, and 3 indicating that no significant concentration of particles in the size range of NLPs were present, consistent with the fact that no structure-directing scaffold protein was added. The corresponding denaturing SDS gel shows protein bands consistent with *P. furiosus* membrane proteins in every fraction. Combined, these gel results show that *P. furiosus* membrane proteins were eluted from the SEC column, but not in the form of NLPs. The lower intensity of the bands in FIG. 2b may be due in part to sample filtration prior to SEC purification, which removed protein-containing fragments larger than ~200 nm in the assemblies. With no scaffold protein present to break up and solubilize the vesicles, assembly B may have contained insoluble or large particles which were removed during the filtration step. It is important to note that assembly A fractions containing substantial protein content eluted at later times from the SEC column compared to assembly B fractions, and were thus smaller in size. this discrepancy in elution time is another indication that addition of the Apo E422k scaffold protein directed the formation of smaller particles compared to those present in the assembly lacking Apo E422k.

Figure 3:
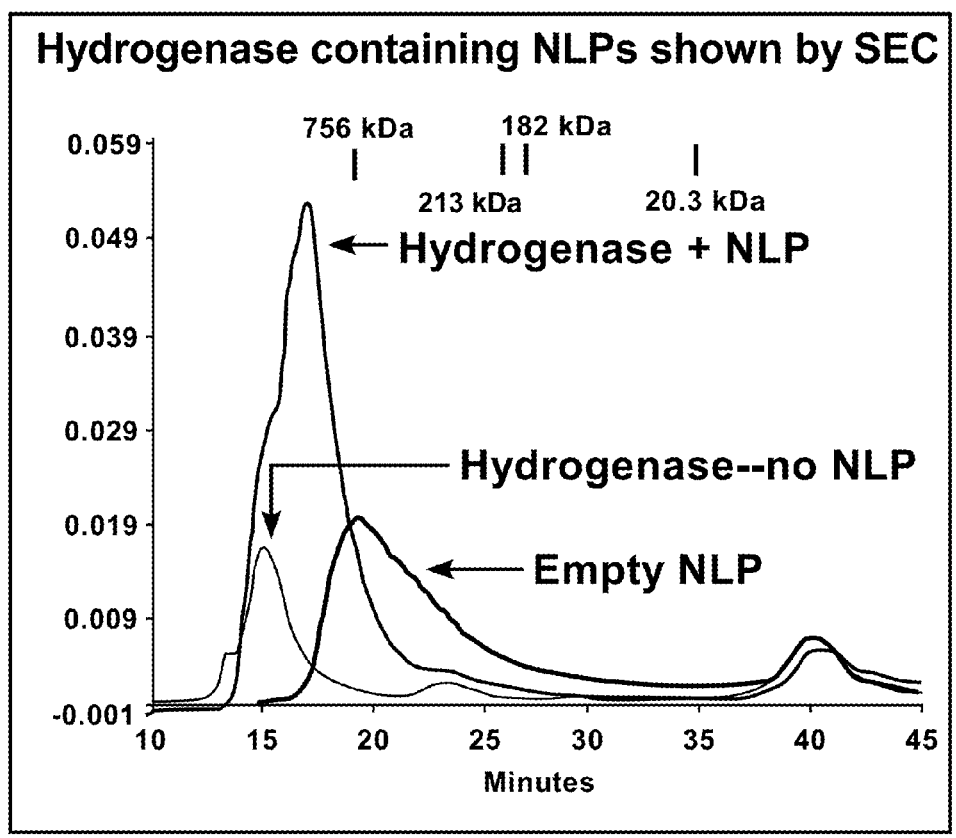
FIG. 3 shows a diagram illustrating an exemplary identification of the nanoliprotein particles of the present disclosure, according to an embodiment herein disclosed. In particular, the figure shows a chart illustrating results of a size exclusion chromatograph of an assembly mixture containing MBH/NLP (Hydrogenase+NLP), hydrogenase (hydrogenase—no NLP) and empty NLP (Empty NLP).

An additional illustration of identification and characterization of MBH/NLP is illustrated in FIG. 3, which shows a size exclusion chromatograph containing 3 peaks. The peaks correspond to components from a crude hydrogenase-NLP assembly that eluted at distinct times and were separated on the basis of size. The chromatograph shows a main peak at about 18 minutes which elutes after the crude membrane peak (hydrogenase-no NLP at 15 minutes) and before the "empty" NLP peak (20 minutes). These results indicate that the assembly mixture containing both crude PF membranes and NLP components resulted in particles of smaller size than the crude membrane suspension, and larger in size than the "empty" NLPs. The results are consistent with the successful assembly of NLPs containing membranes from *P. furiosus*.

Example 3: Characterization of MBH/NLPs: Atomic Force Microscopy

Nanolipoprotein particles were produced and separated from unincorporated free proteins and lipids using size exclusion chromatography (SEC) as exemplified in Example 2. The resulting fractions were characterized for size and homogeneity by native and denaturing gel electrophoresis and atomic force microscopy (AFM).

In particular, gel electrophoresis of the SEC fractions from assembly A support the formation of NLPs containing proteins from the *P. furiosus* solubilized membranes. In order to determine the morphology and size distribution of these particles, the SEC fractions were characterized with AFM. Atomic force microscopy (AFM) was carried out according to published procedures. [16, 17]

Figure 4:
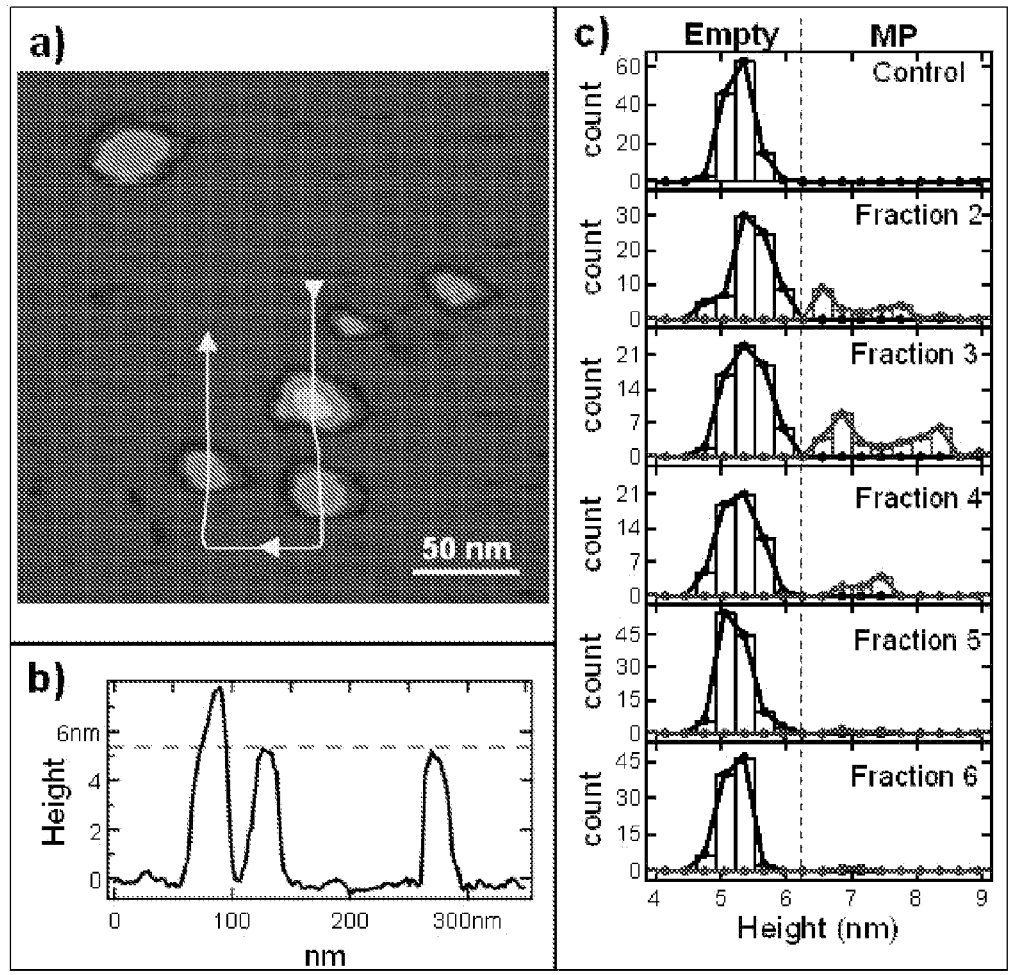
FIG. 4 shows identification of nanoliprotein particles of the present disclosure according to an embodiment herein disclosed. In particular, panel a) shows an AFM image of NLPs from fraction 3 of assembly A shown in FIG. 2. Light gray regions are indicative of particles that are higher than 6.5 nm. Panel b) shows a diagram illustrating height differences between two NLPs from the cross section with line trace shown in panel a). Panel c) shows histograms of heights observed for "empty" NLP (assembled without *P. furiosus* membrane) and size exclusion fractions 2-6 from Assembly A of FIG. 2, assembled with *P. furiosus* membrane.

The results are illustrated in FIG. 4. In particular, FIG. 4a shows a representative AFM image of fraction 3 from assembly A. Round, discrete disk-shaped particles on the order of 20-30 nm in diameter are observed with varied height profiles. The heights of the particles are depicted as variations in the shade of green in the center of each particle. Cross sections of two representative particles (following the superimposed yellow line) are shown in FIG. 4b. As shown by the height profile, the lighter green regions correspond to heights greater than 6.5 nm. Fractions 2, 3, and 4 were found by AFM to consist of nanometer scale discoidal particles with some fraction of the particles determined to be higher than the NLPs in an empty assembly. The height profiles of these fractions are depicted in the histograms of NLP height in FIG. 4c. The top histogram represents the height distributions of empty NLPs, displaying a Gaussian distribution with a mean height of 4.9+/−0.2 nm, consistent with the height of a lipid bilayer. In contrast, assembly A fractions 2, 3, and 4 contain two populations of NLPs: those which have height profiles very similar to those of the empty NLPs, and a population of particles which have significantly "taller" height profiles than the empty NLP subset.

Because P. furiosus~membranes have associated membrane proteins, including MBH, which can both span and extend beyond the cell membrane, the subset of taller NLPs likely contains MBH.

Example 4: Hydrogen Production by MBH/NLPs

The MBH-NLPs produced separated and characterized as exemplified in Example 3, were tested for hydrogen production using an established gas chromatography (GC) assay [11, 12].

In particular, hydrogenase activity was determined by measuring Hz evolution in a gas chromatograph using 2 mM methyl viologen as the electron carrier and 10 mM sodium dithionite as the electron donor.

Figure 5:
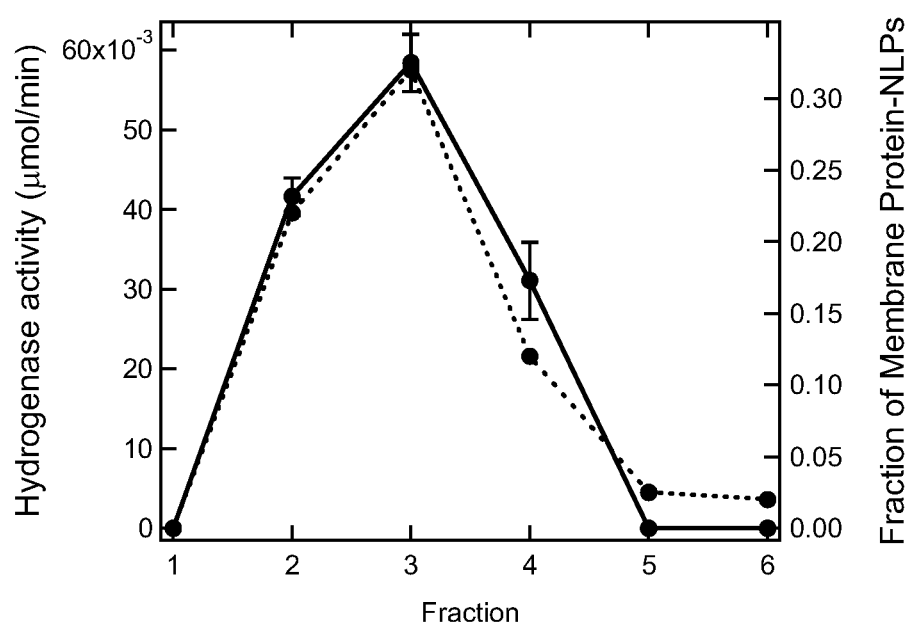
FIG. 5 shows a diagram illustrating hydrogen production performed with MBH nanoparticles according to an embodiment herein disclosed. In particular, the diagram shows the hydrogenase activity (black line) of an NLP here disclosed as a function of NLP size-exclusion fraction. The dotted line shows the corresponding percentage of membrane containing NLPs in each fraction determined by AFM analysis of NLP heights.

The results are illustrated in FIG. 5, which shows a chart reporting hydrogenase activity as a function of NLP fraction. Remarkably, the particles in fractions 2, 3, arid 4 from assembly A were found to generate hydrogen in the presence of methyl viologen, a non-physiological electron carrier, using sodium dithionite, an electron donor, as determined by GC analysis of the head space above the solution. FIG. 5 shows the hydrogen-producing activity of each NLP-containing fraction (left axis), and the corresponding populations of membrane protein-containing NLPs according to AFM (right axis). The amount of hydrogenase activity in each fraction correlated closely with the proportion of apparent P. furiosus membrane-protein containing NLPs.

Incorporation of MBH into NLPs both stabilized the enzyme in a soluble form and appeared to preserve the enzymatic activity. The total hydrogenase activity used for the material loaded onto the SEC column for the MBH-NLP assembly was 0.09 U (in pmol/min) and the total hydrogenase activity recovered from fractions 2, 3, and 4 totaled 0.13 U: (0.042, 0.058, and 0.03 1 U, respectively, shown in FIG. 5). In contrast, fractions from the assembly B, which lacked scaffold protein, had no measurable hydrogenase activity. The lack of activity from assembly B may be due to denaturation of the MBH by the surfactant present in the NLP assembly solution, which may be irreversible in the absence of a stabilizing scaffold protein, rendering the protein more sensitive to oxygen.

Therefore, following the experiments illustrated in FIG. 5, the fraction with the highest percent of membrane protein associated NLPs (fraction 3) also had the highest level of hydrogenase activity. The total units of hydrogenase activity added to the assembly were 0.09 U (pmol/min/ml). The total units of hydrogenase activity recovered exceeded the initial activity, and were 0.13 U.

In the illustration of in FIG. 5, the dotted line shows the corresponding percentage of membrane containing NLPs in each fraction determined by AFM analysis of NLP heights. (These fractions are shown in FIG. 4c) The close correlation between hydrogenase activity and fraction of "tall" particles indicates that the NLPs containing P. furiosus membrane fragments were responsible for the measured hydrogenase activity.

Example 5: Production, Identification and Uses of MBH/NLPs

Figure 6:
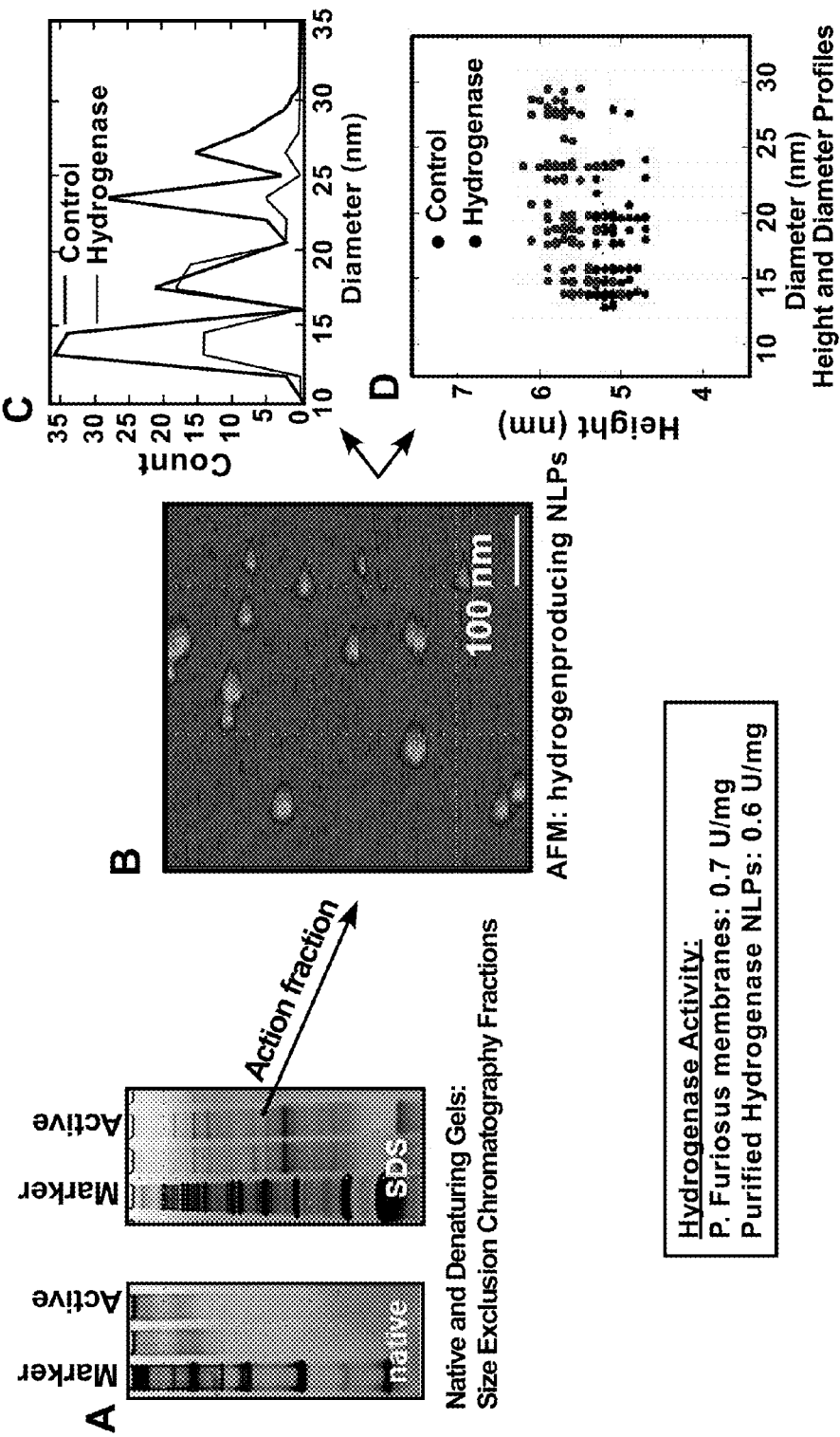
FIG. 6 shows a schematic representation of MBH-NLP and related use for hydrogen production according to an embodiment herein disclosed. In particular, Panel a. shows identification of MBH-NLP by native and denaturing gel electrophoresis. Panel b. comprises imaging of the active MBH-NLP size exclusion chromatography fractions by AFM. Panel c. and d. show size distributions (c) diameter and d) height) of hydrogen producing NLPs compared with empty NLPs.

MBH/NLPs were produced and then identified and used as schematically illustrated in FIG. 6.

Production of MBH/NLPs was performed as follows. Briefly, cellular membranes from P. furiosus lysates were separated from cellular debris and washed using centrifugation (see FIG. 1 and Example 1). A suspension of the membranes was added to a mixture of phospholipid 1,2-dimyristoyl-sn-glycero-3-phosphocholine (DMPC), which mimics cell membrane phospholipids, a truncated amphiphilic apoliprotein E with a mass of 22 kD (Apo E422k) scaffold protein, and cholate, a surfactant used to aid NLP self-assembly.

The mixture was thermally cycled above and below the transition temperature of DMPC to facilitate NLP self-assembly.

Anaerobic conditions were maintained by carrying out the entire NLP assembly process in a PLAS Labs chamber model 855-AC containing 98% argon and 2% hydrogen. Oxygen levels in the chamber were monitored using a Coy Laboratory Products Oxygen and Hydrogen Analyzer, and did not exceed 10 ppm 0 2 over the course of the experiments. Prior to loading in the anaerobic chamber, the DMPC was dissolved in chloroform (100 mg/mL) in a round bottom glass vial. The chloroform was evaporated in a stream of nitrogen to make a uniform lipid film on the vial wall, and placed under vacuum overnight. In the anaerobic chamber, lyophilized E422k was reconstituted to a concentration of 8.3 mg/mL with anaerobic water and the hydrogenase lysate (5.1 mg/mL) was thawed. A typical assembly contained a mass ratio of 4:1:0.05 of DMPC: E422k: P. furiosus membrane at a concentration of 10-20 nig DMPC per mL. First, the dry lipid was reconstituted with anaerobic TBS containing 2 mM sodium dithionite and cholate (20 mM final concentration) under gentle vortex mixing, followed by the addition of P. furiosus membrane and scaffold protein. The particle formation process was initiated using three repeated sets of transition temperature incubations, above and below the transition temperature of DMPC (23.8"C), i.e. 10 minutes at 30° C., then 10 minutes at 20° C. using a thermocycler. Following the temperature cycling, the samples were incubated at 23.8° C. for >20 hours, then dialyzed against four 1000× volumes of TBS over 24 hours.

Purification was performed as follows. The NLPs were purified from free lipid and free protein using size-exclusion chromatography (SEC) using a Superdex 200 HR 10130 colulumn (GE Healthcare) in anaerobic TBS containing 2 mM sodium dithionite at a flow rate of 0.5 mL/minute. Sodium dithionite interferes with absorbance readings at 280 nm, preventing the acquisition of an SEC trace. Fractions were collected in Ar-purged vials. Prior to introduction to the column, the samples were passed through Agilent 0.22 micrometer filters in microcentrifuge tubes.

The particles were then separated from unincorporated free proteins and lipids using size exclusion chromatography (SEC) and the resulting fractions were characterized for size and homogeneity by native and denaturing gel electrophoresis and atomic force microscopy (AFM). The resulting MBH-NLPs were tested for hydrogen production using an established gas chromatography (GC) assay. FIGS. 6c and d represent a comparison of both empty and hydrogenases-containing NLP height and diameter distributions obtained by analyzing AFM images.

Example 6: Production of Immobilized MBH/NLPs

Immobilized MBH/NLP were produced by associating the MBH-NLPs to a support.

In particular, the MBH/NLP assemblies were provided based on the observation that the NLP scaffold protein provides a handle for the eventual immobilization of the enzyme on surfaces for heterogeneous catalysis. Additionally, the presence of the scaffold protein constrains the dimensions of the bilayer and ensures quantized, controllable [16, 17] NLP particle size distributions which are stable and consistent between preparations compared to other model membrane systems, such as inverted vesicles and detergent micelles. For example, artificial vesicles are largely insoluble, and structurally unstable. Furthermore, because vesicles are spherical and therefore contain both an exposed and buried leaflet, a large fraction of the enzymes of interest will have active sites buried inside the vesicle.

Incorporation into lipid nanoparticles is expected to enable the MBH to be immobilized on high surface area porous supports for continuous reactant cycling, and to be tested in a solution phase synthetic enzyme pathways for ex-vivo hydrogen production from biomass.

The ex vivo use of purified cytoplasmic hydrogenases and other compatible enzymes as components of pathways for hydrogen production have been shown to result in several fold higher yields of hydrogen from glucose or starch than in vivo systems, albeit over a limited time scale. Hydrogenase stability in the presence of oxygen, and immobilization for eventual continuous processing, are areas requiring further development. The Applicants used self-assembled, biomimetic lipid nanoparticles as a tool for both solubilizing and stabilizing a unique membrane-bound hydrogenase enzyme with attractive biocatalytic properties. These properties include reversible and low sensitivity to inactivation by oxygen, extremely high thermal and chemical stability, and a remarkable predilection for hydrogen production as opposed to the competing reverse reaction, hydrogen oxidation, in vivo.

Example 7: Hybrid Microbial Fuel Cell Using Bioinspired Molecular Nanolipoprotein Particles A prototype hydrogen production device that is based upon the in vitro reconstitution of hydrogen evolution in microbes has been designed by the Applicants and is depicted in the schematic illustration of FIG. 7.

Figure 7:
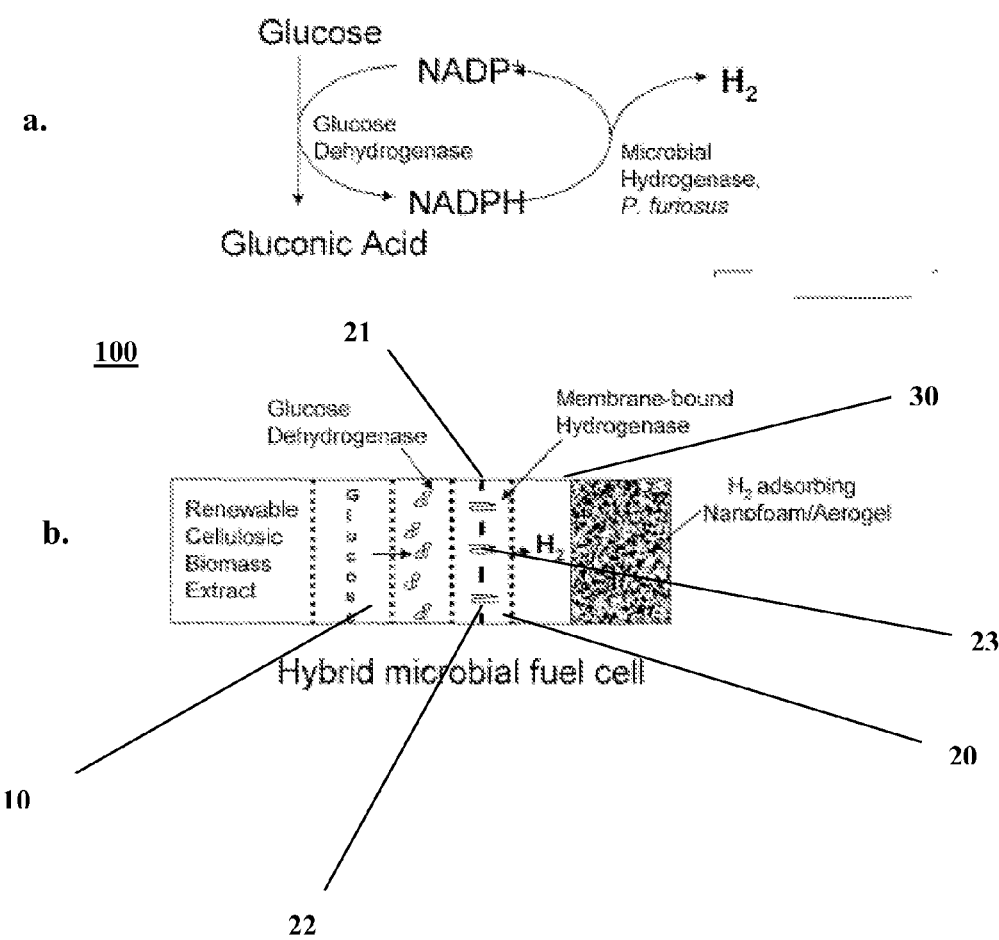

In the illustration of FIG. 7, the device (100) includes a substrate compartment (10), a hydrogenase compartment (20) and a product compartment (30). The substrate compartment (10) and product compartment (30) are further divided in subcompartments.

In the device of FIG. 7, the core system will employ enzymes to form molecular hydrogen from a glucose feedstock; the latter will be generated by an appropriate microbial community breaking down cellulose biomass in the substrate compartment (10). In particular, in the illustration of FIG. 7, glucose dehydrogenase and hydrogenase will act in concert to catalytically cycle NADP+ to NADPH (FIG. 7b). A selected hydrogenase comprised in an MBH-NLP immobilized in the hydrogenase compartment (20) will produce hydrogen via a net two electron and two proton transfer from glucose per reaction cycle.

Production of hydrogen from microbes and the relevant purified enzymes is not currently practical due to low rates of hydrogen evolution from the bacteria and rapid degradation of the hydrogenase enzyme active site. Our design is based on the expectation that sequestration of a functional hydrogenase within a defined membrane bilayer mimetic will significantly reduce active site degradation and enable the construction of a layered device in which each essential components of the system can be optimized for maximum hydrogen production.

In particular, the key component of the device illustrated in FIG. 7, will consist of a thin planar silicon nanopore membrane (21) containing arrays of 20 nm pores (22) that are filled with hydrogenase containing lipid membrane mimetics (23). The mimetic will be nanolipoprotein particles (NLP); these are discoid constructs about 15-20 nm in diameter composed of phospholipids, lipophilic proteins and hydrogenase. The silicon membrane-hydrogenase layer will act as a partition between a buffer containing NADP+/NADPH and glucose dehydrogenase and hydrogen production. This layered redox system will be suspended in a reactor assembly in which one side will be fed by glucose produced by microbial-based hydrolysis of cellulose biomass and the other side will be vented to a hydrogen storage medium. Since the hydrogenase has an equilibrium constant around 1.0, removal of molecular hydrogen from the membrane will drive the reaction to favor product formation and allow far greater efficiency of hydrogen production.

The examples set forth above are provided to give those of ordinary skill in the art a complete disclosure and description of how to make and use the embodiments of the NLPs, methods and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Goldet, G.; Wait, A. F.; Cracknell, J. A,; Vincent, K. A.; Ludwig, M.; Lenz, O.; Friedrich, B.; Armstrong, F. A. *Journal of the American Chemical Society* 2008, 130, (33), 1 1106-1113.
2. Cracknell, J. A.; Vincent, K. A.; Ludwig, M.; Lenz, O.; Friedrich, B.; Armstrong, F. A. *Journal of the American Chemical Society* 2007, 130, 424-425.
3. Kovacs, K. L.; Maroti, G.; Rakhely, G. *International Journal of Hydrogen Energy* 2006, 31, (1 I), 1460-1468.
4. Ho, D.; Chu, B.; Lee, H.; Brooks, E. K.; Kuo, K.; Montemagno, C. D. *Nanotechnology* 2005, 16, (12), 3120-3132.
5. Vincent, K. A.; Cracknell, J. A.; Lenz, O.; Zebger, I.; Friederich, B.; Armstrong, F. *Proceedings of the National Academy of Sciences* 2005, 102, (47), 16951-16954.
6. Zhang, Y.-H. P.; Evans, B. R.; Mielenz, J. R.; Hopkins, R. C.; Adams, M. W. W. *PLoS ONE* 2007, e456, (S), 1-6.
7. Sanderson, K. *Nature* 2008, 452, 400-402.
8. Woodward, J.; Mattingly, S. M.; Danson, M.; Hough, D.; Ward, N.; Adams, M. *Nature Biotechnology* 1996, 14, 872-874.
9. Woodward, J.; Orr, M.; Cordray, K.; Greenbaum, E. *Nature* 2000, 405, 1014-1015.
10. Elgren, T. E.; Zadvorny, O. A.; Brecht, E.; Douglas, T.; Zorin, N. A,; Maroney, M. J.; Peters, *Nano Letters* 2005 Vol. 5, No. 10 2085-2087.
11. Sapra, R.; Bagratnyan, K.; Adams, M. W. W. *Proceedings of the National Academy of Sciences* 2003, 100, (13), 7545-7550.
12. Sapra, R.; Verhagcn, M. F. J. M.; Adams, M. W. W. *Journal of Bacteriology* 2000, 182, (12), 3423-3428.
13. Bayburt, T. H.; Grinkova, Y. V.; Sligar, S. G. *Nano Letters:* 2002, 2, (8), 853-856
14. Bayburt, T. H.; Sligar, S. G. *Protein Science* 2003, 12, 2476-2481
15. Borch, J.; Torta, F.; Sligar, S. G.; RoepstosTf, P. *Analytical Chemistry* 2008, 80, (16), 6245-6252.
16. Blanchette, C. D.; Law, R.; Benner, W. H.; Pesavento, J. B.; Cappuccio, J. A,; Walsworth, V. L.; Kuhn, E. A,; Corzette, M.; Chromy, B. A,; Segelke, B. W.; Coleman, M. A,; Bench, G.; Hoeprich, P. D.; Sulcheck, T. A. *Journal of Lipid Research* 2008, 49, (7), 1420-1430.
17. Chromy, B. A.; Arroyo, E.; Blanchette, C. D.; Bench, G.; Benner, H.; Cappuccio, J. A,; Coleman, M. A.; Henderson, P. T.; Hinz, A. K.; Kuhn, E. A.; Pesavento, J. B.; Segclke, B. W.; Sulcheck, T. A.; Tarasow, T.; Walsworth, V. L.; Hoeprich, P. D. *Journal of the American Chemical Society* 2007, 129, 14348-14354.
18. Nath, A,; Atkins, W. M.; Sligar, S. G. *Biochemistry* 2007, 46, (8), 2059-2069.
19. Boldog, T.; Grimme, S.; Li, M.; Sligar, S.; Hazelbauer, G. L. *Proceedings of the National Academy of Sciences* 2006, 103, (3 1), 1509-1 1514.
20. Leitz, A. J.; Bayburt, T. H.; Basnakov, A. N.; Springer, B. A,; Sligar, S. G. *Biotechniques* 2006, 40, (5), 60 1-6 12.
21. Hedderich, R. *Journal of Bioenergetics and Biomembranes* 2004, 36, (I), 65-75
22. Vignais P M.; Billoud B. Ocurrence, Classification, and Biological Function of Hydrogenases: An overview. *Chemical Reviews* 2007, 107, 4206-4272.
23. Jed O. Eberly and Roger L. Ely *Critical Reviews in Microbiology,* 34:117-130, 2008
24. Sun, X. et al. Membrane-Mimetic Films of Aymmetric Phosphtidylcholine Lipid Bolaamphiphiles. *Langmuir* 2006, 22, 1201-1208
25. Meyer, J. "Fe/Fe hydrogenases and their evolution: a genomic perspective." Cell. Mol. Life. Sci. 64 2007 1063-1084
26. Vincent, K. A. et al. "Investigating and Exploiting the Electrocatalytic Properties of Hydrogenases" Chem. Rev. 2007 107, 4366-4413.
27. Parkin, A., Goldet, G. Cavazza, C. Fontecilla-Camps, J., Armstrong, F. J. Am Chem. Soc. 2008, 13 (40) 13410-13416

What is claimed is:

1. A nanolipoprotein particle comprising
   a membrane associated hydrogenase,
   a membrane forming lipid, and
   a scaffold protein,
   wherein the membrane associated hydrogenase is heteromeric and multimeric; and
   wherein the nanolipoprotein particle further comprises a cell membrane fragment, the cell membrane fragment comprising the membrane associated heteromeric and multimeric hydrogenase in a catalytically active form, the membrane forming lipid and the scaffold protein are at a mass ratio between 1:1 and 20:1 and the scaffold protein and the membrane associated heteromeric and multimeric hydrogenase are at a mass ratio between 1:0.025 and 1:1.

2. The nanolipoprotein particle of claim 1, wherein the membrane associated hydrogenase is a [Ni/Fe] hydrogenase or a [Fe/Fe] hydrogenase.

3. The nanolipoprotein particle of claim 1, wherein the membrane associated hydrogenase is a [Ni/Fe] hydrogenase from *Allochromatium vinosum, Methanosarcina barkeri, Escherichia coli,* and *Rhodospirillum rubrum Desulfomicrobium baculatum* and *Ralstonia* species.

4. The nanolipoprotein particle of claim 1, wherein the membrane associated hydrogenase is a [Ni/Fe] hydrogenase from *Pyrococcus Furiosus.*

5. A biocatalyst assembly comprising the nanolipoprotein particle of claim 1, wherein the nanolipoprotein particle is immobilized to a support.

6. The biocatalyst assembly of claim 5, wherein the support is a solid support.

7. The biocatalyst assembly of claim 5, wherein the support is an electrically conductive support.

8. A method to perform a chemical reaction catalyzed by a membrane associated hydrogenase, the method comprising:
   providing reagents for performing said chemical reaction,
   providing the nanolipoprotein particle of claim 1, wherein the membrane associated hydrogenase is the membrane associated hydrogenase catalyzing the chemical reaction; and
   contacting the reagents with the nanolipoprotein particle for a time and under conditions to allow the reaction to occur, thus performing said chemical reaction.

9. The method of claim 8 wherein the nanolipoprotein particle is immobilized on a solid support.

10. The method of claim 8, wherein the chemical reaction is hydrogen production.

11. The method of claim 10 wherein the hydrogen production is performed as a solution phase reaction.

12. The method of claim 10, wherein the conditions include a temperature between from about 25 degrees C. and about 95 degrees C.

13. The method of claim 8, wherein the membrane associated hydrogenase is a [Ni/Fe] hydrogenase.

14. The method of claim 8, wherein the chemical reaction is oxidation of molecular hydrogen.

15. A system to perform a chemical reaction catalyzed by a membrane associated hydrogenase, the system comprising:
the nanolipoprotein particle of claim 1, wherein the membrane associated hydrogenase is the membrane associated hydrogenase catalyzing the chemical reaction; and
reagents for performing the chemical reaction,
wherein the nanolipoprotein particle and the reagents can be contacted for a time and under conditions to allow the chemical reaction catalyzed by said membrane associated hydrogenase to occur.

16. The system of claim 15, wherein the membrane associated hydrogenase is immobilized to a support.

17. The system of claim 15, wherein the membrane associated hydrogenase is a [Ni/Fe] hydrogenase from *Allochromatium vinosum, Methanosarcina barkeri, Escherichia coli, Rhodospirillum rubrum, Desulfomicrobium baculatum* and *Ralstonia* species.

18. The system of claim 15, wherein the membrane associated hydrogenase is a [Ni/Fe] hydrogenase from *Pyrococcus Furiosus*.

19. A device for performing a chemical reaction catalyzed by a membrane associated hydrogenase, the device comprising:
a substrate compartment, a hydrogenase compartment, and a product compartment, with the substrate compartment in communication with the product compartment through the hydrogenase compartment,
wherein
the hydrogenase compartment comprises the biocatalyst assembly of claim 5; and
the substrate compartment is configured to comprise a substrate for the chemical reaction catalyzed by the membrane associated hydrogenase and to allow contact between said substrate and said membrane associated hydrogenase.

20. The device of claim 19, further comprising a product compartment in communication with the hydrogenase compartment, the product compartment configured to comprise hydrogen produced following the reaction of a substrate with the membrane associated hydrogenase.

21. A nanolipoprotein particle comprising
a membrane associated hydrogenase,
a membrane forming lipid, and
a scaffold protein,
wherein the membrane associated hydrogenase is heteromeric and multimeric in a catalytically active form; and
wherein the nanolipoprotein particle is obtained from a cell membrane fragment, the cell membrane fragment comprising the membrane associated heteromeric and multimeric hydrogenase,
the membrane forming lipid and the scaffold protein are at a mass ratio between 1:1 and 20:1 and the scaffold protein and the membrane associated heteromeric and multimeric hydrogenase are at a mass ratio between 1:0.025 and 1:1.

22. The nanolipoprotein particle of claim 1, wherein the membrane forming lipid is dimyristoylphosphatidylcholine (DMPC), the scaffold protein is Apo E422K, and the DMPC, Apo E422K and the membrane associated heteromeric and multimeric hydrogenase have a mass ratio of about 4:1:0.05.

23. The nanolipoprotein particle of claim 21, wherein the membrane forming lipid is dimyristoylphosphatidylcholine (DMPC), the scaffold protein is Apo E422K, and the DMPC, Apo E422K and the membrane associated heteromeric and multimeric hydrogenase have a mass ratio of about 4:1:0.05.

* * * * *

UNITED STATES PATENT AND TRADEMARK OFFICE
CERTIFICATE OF CORRECTION

PATENT NO. : 9,688,718 B2
APPLICATION NO. : 12/352472
DATED : June 27, 2017
INVENTOR(S) : Sarah E. Baker et al.

Page 1 of 1

It is certified that error appears in the above-identified patent and that said Letters Patent is hereby corrected as shown below:

In the Specification

In the body of the text, under the title "STATEMENT OF GOVERNMENT GRANT", Column 1, Lines 34-37, delete the paragraph "The U.S. Government has rights in this invention pursuant to Contract No. Contract No. DE-AC52-07 NA27344 between the U.S. Department of Energy and Lawrence Livermore National Security, LLC." and replace with the paragraph "The United States Government has rights in this invention pursuant to Contract No. DE-AC52-07NA27344 between the United States Department of Energy and Lawrence Livermore National Security, LLC, for the operation of Lawrence Livermore National Laboratory."

Signed and Sealed this
Nineteenth Day of February, 2019

Andrei Iancu
*Director of the United States Patent and Trademark Office*